United States Patent
Rix et al.

(10) Patent No.: US 7,601,666 B2
(45) Date of Patent: Oct. 13, 2009

(54) OLEFIN POLYMERIZATION CATALYST SYSTEM AND PROCESS FOR USE THEREOF

(75) Inventors: Francis C. Rix, League City, TX (US); Smita Kacker, Houston, TX (US); Sudhin Datta, Houston, TX (US); Rul Zhao, Houston, TX (US); Vetkav R. Eswaran, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 386 days.

(21) Appl. No.: 11/178,147

(22) Filed: Jul. 8, 2005

(65) Prior Publication Data

US 2006/0009595 A1 Jan. 12, 2006

Related U.S. Application Data

(60) Provisional application No. 60/586,465, filed on Jul. 8, 2004.

(51) Int. Cl.
*C07F 17/00* (2006.01)
*C08F 4/6592* (2006.01)
*C08F 4/642* (2006.01)
*C08F 4/643* (2006.01)

(52) U.S. Cl. .............. 502/117; 556/7; 556/11; 556/12; 556/13; 556/27; 556/53; 526/127; 526/134; 526/160; 526/170; 526/943; 502/152

(58) Field of Classification Search ......... 556/7, 556/11, 12, 13, 27, 53; 502/117, 152; 526/127, 526/134, 160, 170, 943

See application file for complete search history.

(56) References Cited

U.S. PATENT DOCUMENTS

| 5,700,886 A | 12/1997 | Winter et al. | 526/119 |
| 6,034,022 A | 3/2000 | McAdon et al. | 502/103 |
| 6,051,522 A | 4/2000 | Rohrmann et al. | 502/103 |

(Continued)

FOREIGN PATENT DOCUMENTS

| DE | 19823168 | 11/1999 |
| EP | 0645401 | 3/1995 |
| EP | 1138687 | 10/2001 |
| WO | 98/13393 | 4/1998 |
| WO | 99/40129 | 8/1999 |
| WO | 99/43717 | 9/1999 |
| WO | 00/12565 | 3/2000 |
| WO | 00/25916 | 5/2000 |
| WO | 00/26266 | 5/2000 |
| WO | 02/01745 | 1/2002 |
| WO | 02/44260 | 6/2002 |
| WO | 02/083753 | 10/2002 |
| WO | 2004/050724 | 6/2004 |

OTHER PUBLICATIONS

Lee et al., "Electronic Effects in Ziegler-Natta Polymerization of Propylene and Ethylene Using Soluble Metallocene Catalysts", Organometallics 1992, 11, 2115-2122.
Resconi et al., "Synthesis of Atactic Polypropylene Using Metallocene Catalysts", Metallocene-based Polyolefins, Eds. J. Scheirs, W. Kaminsky, Wiley, NY 2000, 467-484.
Resconi et al., "Selectivity in Propene Polymerization with Metallocene Catalysts", Chem. Rev. 2000, 100, 1253-1345.

*Primary Examiner*—Roberto Rábago

(57) ABSTRACT

A compound represented by the formula:

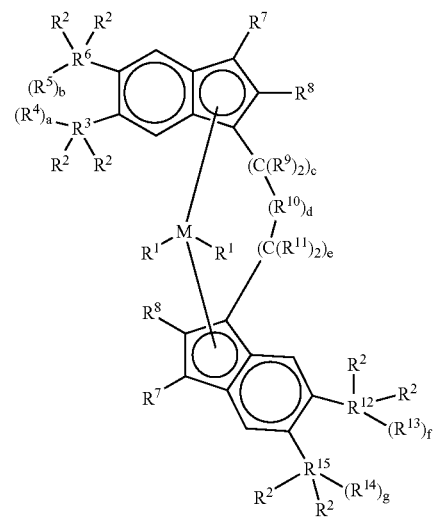

where:
M is a transition metal selected from group 4 of the periodic table;
each $R^1$ is independently selected from the group consisting of hydrogen, hydrocarbyl, substituted hydrocarbyl and functional group, and any two $R^1$ groups may be linked, provided that if the two $R^1$ groups are linked, then they do not form a butadiene group when M is Zr; $R^3$ is carbon or silicon; $R^4$ is hydrogen, hydrocarbyl, substituted hydrocarbyl or a functional group; $R^5$ is hydrogen, hydrocarbyl, substituted hydrocarbyl or a functional group, $R^4$ and $R^5$ may be bound together to form a ring; $R^6$ is carbon or silicon; each $R^7$ is hydrogen; each $R^8$ is independently selected from the group consisting of hydrogen, methyl, ethyl, propyl, butyl, pentyl, hexyl and the isomers thereof; $R^{10}$ is $-M^2(R^{16})_n-$ where $M^2$ is B, Al, N, P, Si or Ge, h is 1 or 2; each $R^9$, $R^{11}$, $R^{13}$ and $R^{14}$ and $R^{16}$ is hydrogen, hydrocarbyl, substituted hydrocarbyl or a functional group, and two $R^{16}$ groups may be linked together to form a ring; each $R^{12}$ and $R^{15}$ is carbon or silicon; and a, b, c, d, e, f, and g are independently 0, 1, or 2.

16 Claims, No Drawings

U.S. PATENT DOCUMENTS

| | | | |
|---|---|---|---|
| 6,057,408 A | 5/2000 | Winter et al. | 526/160 |
| 6,084,115 A * | 7/2000 | Chen et al. | 556/22 |
| 6,143,686 A | 11/2000 | Vizzini et al. | 502/152 |
| 6,228,795 B1 | 5/2001 | Vizzini et al. | 502/155 |
| 6,268,444 B1 | 7/2001 | Klosin et al. | 526/127 |
| 6,391,989 B1 | 5/2002 | Bohnen et al. | 526/134 |
| 6,469,188 B1 | 10/2002 | Miller et al. | 556/12 |
| 6,479,424 B1 | 11/2002 | Ernst et al. | 502/152 |
| 6,482,902 B1 | 11/2002 | Bohnen et al. | 526/127 |
| 6,525,157 B2 | 2/2003 | Cozewith et al. | 526/348 |
| 6,576,306 B2 | 6/2003 | Mehta et al. | 428/35.5 |
| 6,583,227 B2 | 6/2003 | Mehta et al. | 525/240 |
| 2002/0004575 A1 | 1/2002 | Cozewith et al. | 526/348 |
| 2006/0052553 A1* | 3/2006 | Resconi et al. | 526/127 |

* cited by examiner

US 7,601,666 B2

OLEFIN POLYMERIZATION CATALYST SYSTEM AND PROCESS FOR USE THEREOF

PRIORITY CLAIM & CROSS-REFERENCE TO RELATED APPLICATIONS

This application claims the benefit of Provisional Application No. 60/586,465 filed Jul. 8, 2004, the disclosure of which is incorporated by reference.

FIELD OF THE INVENTION

This invention relates to novel transition metal compounds and to processes to polymerize or oligomerize unsaturated monomers using these transition metal compounds and polymers or oligomers produced therefrom.

BACKGROUND OF THE INVENTION

Various processes and catalysts exist for the homopolymerization or copolymerization of unsaturated monomers, particularly the polymerization of olefins. For many applications, it is desirable for a polyolefin to have a high weight average molecular weight while having a relatively narrow molecular weight distribution. Chiral bis-indenyl metallocene catalysts have been used to prepare highly crystalline isotatic polypropylene and copolymers of propylene and other monomers (Resconi, L. Chem. Rev. 2000, 100, 1253). Non-chiral metallocene catalysts have also been prepared which yield atactic polypropylene and copolymers (Resconi, L. in Metallocene Based Polyolefins, Eds. J. Schiers, W. Kaminsky; Wiley; NY, 2000; 467). While, there are chiral catalysts which operate between these extremes, yielding polypropylene with crystallinity less than highly crystalline and more than amorphous, generally these chiral catalysts give low molecular weight polymer. This is also true for copolymers prepared from propylene and other monomers, using such systems.

U.S. Pat. No. 6,051,522 describes bridged chiral metallocenes as catalysts useful for olefin polymerization. WO2002/01745, US 2002/0004575A1, WO2002/083753A1, and U.S. Pat. No. 6,525,157 disclose processes for the preparation of a propylene/ethylene copolymer containing tacticity within the propylene sequences using the chiral metallocene rac-Me$_2$Si(1-indenyl)$_2$HfMe$_2$ and an ionizing activator. U.S. Pat. No. 6,057,408 discloses a process for the preparation of high molecular weight propylene/ethylene copolymers with high crystallinity in the propylene sequences using chiral bis-indenyl metallocenes. The catalyst that yielded the highest molecular weight copolymer was rac-Me$_2$Si(2-Me-4-(1-napthyl)-1-indenyl)$_2$ZrCl$_2$.

S. Collins and coworkers reported (Organometallics 1992, 11, 2115) a study of the effect of substituents in the 5,6-positions on a series of chiral ethylene bridged metallocenes, rac-(CH$_2$CH$_2$)(5,6-X$_2$-1-indenyl)$_2$ZrCl$_2$, on solution ethylene and propylene polymerizations. In comparing X═H and X═Me, similar molecular weights were found for the preparation of polyethylene (X═H, Mn=145 Kg/mol; X═Me, Mn=127 Kg/mol) and polypropylene (X═H, Mn=15.7 Kg/mol; X═Me, Mn=16 Kg/mol). Likewise, In U.S. Pat. No. 5,455,365, chiral bis-indenyl metallocenes containing methyl groups in the 5 and 6 positions and metallocenes containing a phenyl group in the 5 or 6 position are disclosed. Polymerizations at 70° C. in liquid propylene gave moderately crystalline polypropylene, as evidenced by polymer melting points between 132 and 147° C. The molecular weights (Mw) of these materials are between 100 and 200 Kg/mol. Copolymerization of propylene with ethylene, using rac-Me$_2$Si(2,5,6-Me$_3$-1-indenyl)ZrCl$_2$/MAO, yielded a 2.8 wt % ethylene, 97.2 wt % propylene copolymer with a significantly lower molecular weight as evidenced by a drop in intrinsic viscosity from 155 mL/g (Mw=143 Kg/mol) to 98 mL/g (Mw not recorded). This copolymerization also gave a decrease in melting point from 132 to 123° C.

In U.S. Pat. No. 6,084,115, a chiral bis-indenyl metallocene containing an annulated tetramethylated cyclohexyl ring attached at the 5 and 6 positions is disclosed. This metallocene, rac -Me$_2$Si(5,6,7,8-tetrahydro-2,5,5,8,8-pentamethyl-benz[f]indenyl)$_2$Zr(1,4-diphenylbutadiene), is reported to be in the +2 oxidation state. Propylene polymerization behavior was reported in alkane solution (24 wt % propylene) under a partial pressure of hydrogen at 70° C. Molecular weights obtained were ca. 60 Kg/mol and polymer melting points were 144.8-147° C. These molecular weights were lower than the analogous complex with H in the 5 and 6 positions, rac -Me$_2$Si(2-Me-1-indenyl)Zr(1,4-diphenylbutadiene), Mw=79 Kg/mol. Similar results observed in ethylene/octene polymerizations with these two catalysts. No H$_2$-free solution polymerizations were reported. Supported catalysts were also examined in this patent, however broad molecular weight distributions (>3.5) make comparisons between catalysts difficult. These results indicate that a molecular weight advantage is not expected for catalysts with large groups in the 5 and 6 positions. Thus, no meaningful increase in polymer molecular weight can be ascribed to these previous substitutions.

WO 2004/050724 discloses polymerization of butene with methylalumoxane and dimethylsilyl bis[2-methyl-5,6(tetramethyl-cyclotrimethylen)indenyl]zirconium dichloride and also described certain indenyl type compounds with annulated six membered rings; however, WO 2004/050724 does not obtain higher molecular weights at higher temperatures.

Thus there is a need in the art to provide catalyst systems that can provide polymers having high molecular weight as well as good crystallinity preferably prepared at higher temperatures and productivities than otherwise possible.

U.S. Pat. No. 6,479,424 discloses the preparation of unbridged species bis(2-(3,5-di-t-butylphenyl)-5,5,8,8-tetramethyl-5,6,7,8-tetrahydrobenz(f)indenyl) hafnium dichloride, bis(2-(3,5-di-t-butylphenyl)-5,5,8,8-tetramethyl-5,6,7,8-tetrahydrobenz(f)indenyl)zirconium dichloride, bis(2-(4-t-butylphenyl)-5,5,8,8-tetramethyl-5,6,7,8-tetrahydrobenz(f)indenyl)hafnium dichloride, and bis(2-(4-t-butylphenyl)-5,5,8,8-tetramethyl-5,6,7,8-tetrahydrobenz(f)indenyl)zirconium dichloride which are used to produce propylene polymers.

Other references of interest include: 1) U.S. Pat. No. 6,034,022, (particularly example 17); 2) U.S. Pat. No. 6,268,444, (particularly example 2); 3) U.S. Pat. No. 6,469,188; and 4) EP 1 138 687, (particularly examples 8 and 9).

Further, there is a need in the art to provide processes to produce propylene based polymers having higher molecular weights at higher temperatures, preferably in solution processes. Likewise, there is a need in the art to provide processes to produce propylene based polymers having higher molecular weights at higher temperatures in solution processes using a non-coordinating anion activator, where the propylene concentration in the feed is lower.

SUMMARY OF THE INVENTION

This invention relates to a transition metal catalyst compound represented by the formula 1:

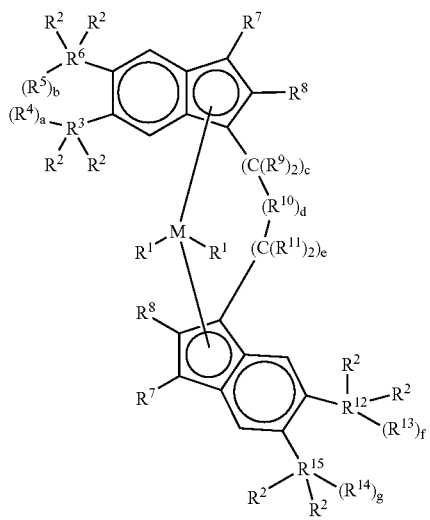

where

M is a transition metal selected from group 4 of the periodic table;

each $R^1$ is independently selected from the group consisting of hydrogen, hydrocarbyl, substituted hydrocarbyl and functional group, and any two $R^1$ may be linked;

each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof;

$R^3$ is carbon or silicon;

$R^4$ is hydrogen, hydrocarbyl, substituted hydrocarbyl or a functional group;

a is 0, 1, or 2;

$R^5$ is hydrogen, hydrocarbyl, substituted hydrocarbyl or a functional group, $R^4$ and $R^5$ may be bound together to form a ring, and $R^5$ and $R^3$ may be bound together to form a ring;

b is 0, 1, or 2;

$R^6$ is carbon or silicon; and $R^4$ and $R^6$ may be bound together to form a ring;

each $R^7$ is hydrogen;

each $R^8$ is independently selected from the group consisting of hydrogen, methyl, ethyl, propyl, butyl, pentyl, hexyl and the isomers thereof;

each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{16}$ may be linked together to form a ring, $R^9$ and $R^{11}$ may be linked together to form a ring;

c is 0, 1 or 2;

$R^{10}$ is -$M^2(R^{16})_h$— where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;

d is 0, 1, or 2;

each $R^{11}$ is independently selected from the group consisting of hydrogen, hydrocarbyl, substituted hydrocarbyl and a functional group, and two $R^{11}$ groups may be linked together to form a ring, and $R^{11}$ and $R^8$ may be linked together to form a ring, and $R^{11}$ and $R^{16}$ may be linked together to form a ring;

e is 0, 1, or 2;

where the sum of c, d, and e is 1, 2 or 3;

$R^{12}$ is carbon or silicon;

$R^{13}$ is hydrogen, hydrocarbyl, substituted hydrocarbyl or a functional group, and $R^{13}$ and $R^{14}$ may be bound together to form a ring, and $R^{13}$ and $R^{15}$ may be bound together to form a ring, when g is 0;

f is 0, 1, or 2;

$R^{14}$ is hydrogen, hydrocarbyl, substituted hydrocarbyl or a functional group, and $R^{14}$ and $R^{12}$ may be bound together to form a ring, when f is 0;

g is 0, 1, or 2; and $R^{15}$ is carbon or silicon;

provided that if the two $R^1$ groups are linked, then they do not form a butadiene group when M is Zr.

This invention further relates to a process to polymerize unsaturated monomers using the above compositions, optionally combined with an activator.

DETAILED DESCRIPTION

This invention relates to a new class of catalyst compounds that may be combined with one or more activators to polymerize any unsaturated monomer.

For the purposes of this invention and the claims thereto when a polymer is referred to as comprising a monomer, the monomer present in the polymer is the polymerized form of the monomer. For the purposes of this invention and the claims thereto when a polymer is referred to as comprising an olefin, the olefin present in the polymer is the polymerized form of the olefin. In the description herein the transition metal catalyst compound may be described as a catalyst precursor, a pre-catalyst compound, a transition metal complex or a catalyst compound, and these terms are used interchangeably. A catalyst system is a combination of a transition metal catalyst compound and an activator. An activator is also interchangeably referred to as a cocatalyst. In addition, a reactor is any container(s) in which a chemical reaction occurs.

As used herein, the numbering scheme for the Periodic Table Groups is the new notation as set out in CHEMICAL AND ENGINEERING NEWS, 63(5), 27 (1985).

Further for purposes of this invention Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, Ph is phenyl, and TMS is trimethylsilyl.

This invention relates to the preparation of polyolefins in solution, slurry or gas phase processes using chiral metallocenes containing specifically substituted indenyl ligands, (such as those represented by Formula 1 above), in combination with an activator and optionally an additional cocatalyst. In one embodiment of this invention, polyalpha-olefins are prepared. In another embodiment, olefin copolymers, substantially free of diene are prepared. In a preferred embodiment of this invention, polypropylene with intermediate crystallinity and high molecular weight is prepared (intermediate crystallinity is defined to be having a percent crystallinity of 15 to 35% as measured by DSC procedure described below and high molecular weight is defined to be an Mw above 100,000 as measured by GPC using polystyrene standards). Such polymers are preferably for use in applications such as plasticizer and lubricant formulations, hot melt adhesive applications, coatings, seals, insulation, molding compositions or sound insulating materials. Another preferred embodiment of this invention is the preparation of propylene/ethylene copolymers containing tacticity within the propylene sequences as described in WO2002/01745, US2002/0004575A1, WO2002/083753A1, U.S. Pat. No. 6,525,157B2. Such propylene/ethylene copolymers have utility as thermoplastic elastomers, impact modifiers, compatibilizers in thermoplastic polyolefins, elastic fibers and films, dynamically vulcanizable alloys, curable elastomers, adhesives, PVC replacements and viscosity modifiers. Also, blends of such copolymers with polypropylene, upon orientation give significantly enhanced elastic recovery and tensile strength. Preferred catalyst systems comprising a metallocene represented by Formula 1, an activator and optionally an additional cocatalyst are particularly suited for preparing polyolefins of high molecular weight at industrially useful temperatures.

Differential scanning calorimetric (DSC) trace data is obtained using a TA Instruments model 2920 machine. Samples weighing approximately 7-10 mg are sealed in aluminum sample pans. The DSC data are recorded by first cooling the sample to −50° C. and then gradually heating it to 200° C. at a rate of 10° C./minute. The sample is kept at 200° C. for 5 minutes before a second cooling-heating cycle is applied. Both the first and second cycle thermal events are recorded. Areas under the melting curves are measured and used to determine the heat of fusion and the degree of crystallinity. The percent crystallinity is calculated using the formula, [area under the curve (Joules/gram)/B (Joules/gram)]*100, where B is the heat of fusion for the homopolymer of the major monomer component. These values for B are to be obtained from the Polymer Handbook, Fourth Edition, published by John Wiley and Sons, New York 1999. A value of 189 J/g (B) is used as the heat of fusion for polypropylene.

This invention further relates to processes for preparing oligomers and/or polymers of unsaturated monomers, such as polar monomers and or olefins comprising contacting a transition metal compound (as described herein) and, optionally, an activator with the monomers. This invention also relates to a process for the preparation of olefin polymers and copolymers using metallocenes containing specifically substituted indenyl ligands as represented in Formula 1:

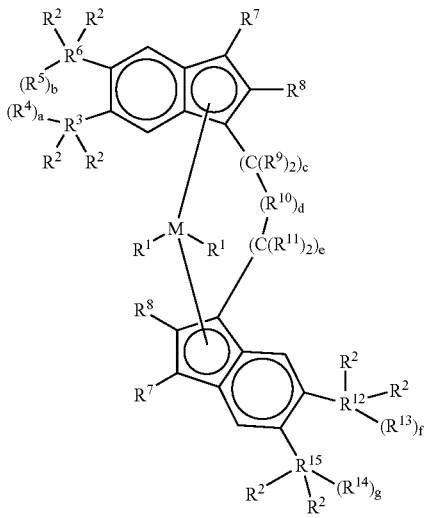

where:
M is a transition metal selected form group 4 of the periodic table, preferably Zr or Hf, most preferably Hf;

each $R^1$ is independently selected from the group consisting of hydrogen, hydrocarbyl, substituted hydrocarbyl and a functional group, preferably, $R^1$ is hydrogen, a hydrocarbon or a halide, preferably $R^1$ is a hydride, even more preferably $R^1$ is selected from the group consisting of methyl, ethyl, trimethylsilylmethyl, trimethylsilyl, phenyl, naphthyl, allyl, and benzyl; even more preferably, $R^1$ is methyl, and $R^1$ may be linked, and the $R^1$ groups may be the same or different;

each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof, preferably $R^2$ is methyl, ethyl or propyl, more preferably, $R^2$ is methyl, and the $R^2$ groups may be the same or different;

$R^3$ is carbon or silicon;

$R^4$ is hydrogen, hydrocarbyl, substituted hydrocarbyl or a functional group, preferably $R^4$ is $CH_2$, and $R^4$ and $R^5$ may be bound together to form a ring, and or $R^4$ and $R^6$ may be bound together to form a ring;

a is an integer that is equal to 0, 1, or 2;

$R^5$ is hydrogen, hydrocarbyl, substituted hydrocarbyl or a functional group, preferably $R^5$ is $CH_2$, and $R^5$ and $R^3$ may be bound together to form a ring;

b is an integer that is equal to 0, 1, or 2;

$R^6$ is carbon or silicon;

each $R^7$ hydrogen;

each $R^8$ is independently selected from the group consisting of hydrogen, methyl, ethyl, propyl, butyl, pentyl, hexyl and the isomers thereof, preferably $R^8$ is hydrogen, methyl, ethyl or propyl, more preferably $R^8$ is hydrogen or methyl, and the $R^8$ groups may be the same or different;

each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{16}$ may be linked together to form a ring, and $R^9$ and $R^{11}$ may be linked together to form a ring;

$R^{10}$ is $-M^2(R^{16})_h-$ where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is $SiMe_2$, $Si(CH_2)_2$, $Si(CH_2)_3$, $SiPh_2$, $Si(biphenyl)_1$, $Si(biphenyl)_2$, $Si(o-tolyl)_2$, more preferably $R^{10}$ is $SiMe_2$ or $SiPh_2$;

each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring, and $R^{11}$ and $R^{16}$ may be linked together to form a ring;

c is an integer=0, 1, or 2;
d is an integer=0, 1, or 2;
e is an integer=0, 1, or 2;
The sum of c, d, and e is 1, 2 or 3, preferably the sum of c, d, and e is 1 or 2, more preferably, the sum of c, d, and e is 1;

$R^{12}$ is carbon or silicon;

$R^{13}$ is hydrogen, hydrocarbyl, substituted hydrocarbyl or a functional group, preferably $CH_2$, and $R^{13}$ and $R^{14}$ may be bound together to form a ring, and $R^{13}$ and $R^{15}$ may be bound together to form a ring, when g is 0;

$R^{14}$ is hydrogen, hydrocarbyl, substituted hydrocarbyl or a functional group, preferably $CH_2$, and $R^{14}$ and $R^{12}$ may be bound together to form a ring when f is 0;

$R^{15}$ is carbon or silicon;

f is an integer that is equal to 0, 1, or 2;

g is an integer that is equal to 0, 1, or 2, provided that if the two $R^1$ groups are linked, then they do not form a butadiene group when M is Zr.

In a preferred embodiment, $R^3$ and $R^6$ do not form a 5 carbon ring. In an alternate embodiment, and or $R^{12}$ and $R^{15}$ do not form a 5 carbon ring. In an alternate embodiment $R^3$ and $R^6$ and $R^{12}$ and $R^{15}$ do not form a 5 carbon ring.

In a preferred embodiment, $R^3$ and $R^6$ do not form a 5 carbon ring when M is Zr. In an alternate embodiment, and or $R^{12}$ and $R^{15}$ do not form a 5 carbon ring when M is Zr. In an alternate embodiment $R^3$ and $R^6$ and $R^{12}$ and $R^{15}$ do not form a 5 carbon ring when M is Zr.

In a preferred embodiment when M is Hf, $R^3$ and $R^6$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In an alternate embodiment, when M is Hf, $R^{12}$ and $R^{15}$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In another preferred embodiment, M is Hf, and both $R^1$ groups are methyl.

Substituted hydrocarbyl radicals (also called substituted hydrocarbyls) are radicals in which at least one hydrocarbyl hydrogen atom has been substituted with at least one heteroatom or heteroatom containing group.

The term "hydrocarbyl radical" is sometimes used interchangeably with "hydrocarbyl" throughout this document. For purposes of this disclosure, "hydrocarbyl radical" encompasses radicals containing carbon, hydrogen and optionally silicon atoms, preferably 1 to 100 carbon atoms, hydrogen and optionally silicon. These radicals can be linear, branched, or cyclic including polycyclic. These radicals can be saturated, partially unsaturated or fully unsaturated, and when cyclic, may be aromatic or non-aromatic.

Hydrocarbyls may be arenes. An arene is a substituted or unsubstituted aromatic hydrocarbon. Arenes may be monocyclic, polycyclic, hydrocarbon ring assemblies or fused ring systems. Arenes may be substituted or unsubstituted. Substituted hydrocarbyls may be arenes containing functional groups. As such, substituted hydrocarbyls may be heterocyclics, polyheterocyclics, heterocyclic ring assemblies or fused heterocyclic ring systems.

In some embodiments, the hydrocarbyl radical is selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Functional groups are heteroatoms of groups 1-17 of the periodic table either alone or connected to other elements by covalent or other interactions such as ionic, van der Waals forces, or hydrogen bonding. Examples of functional groups include fluoride, chloride, bromide, iodide, carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica.

In a preferred embodiment, the catalyst compounds used herein are represented by the Formula 2:

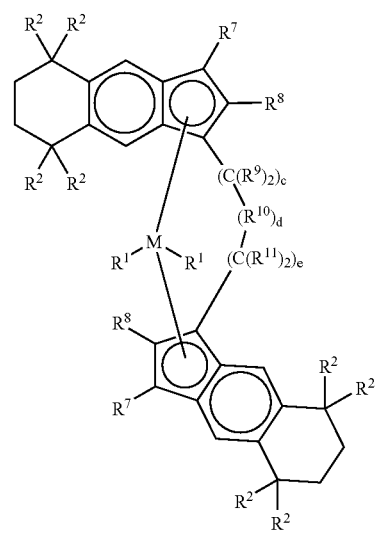

where:
M is a transition metal selected from group 4 of the periodic table, preferably Zr or Hf, most preferably Hf;
each $R^1$ is independently selected from the group consisting of hydrogen, hydrocarbyl, substituted hydrocarbyl and a functional group, preferably $R^1$ is a hydrogen, a hydrocarbon or a halide, more preferably $R^1$ is a hydride, methyl, ethyl, trimethylsilylmethyl, trimethylsilyl, phenyl, naphthyl, allyl, or benzyl, even more preferably $R^1$ is methyl, and the two $R^1$ groups may be the same or different, and the two $R^1$ groups may be linked;
each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof, preferably $R^2$ is methyl, ethyl or propyl, more preferably, $R^2$ is methyl, and the $R^2$ groups may be the same or different;
each $R^7$ is hydrogen;
each $R^8$ is independently selected from the group consisting of hydrogen, methyl, ethyl, propyl, butyl, pentyl, hexyl and the isomers thereof, preferably $R^8$ is hydrogen, methyl, ethyl or propyl, more preferably, $R^8$ is hydrogen or methyl, and the $R^8$ groups may be the same or different;
each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{11}$ may be linked together to form a ring;
$R^{10}$ is $-M^2(R^{16})_h-$ where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is $SiMe_2$, $Si(CH_2)_2$, $Si(CH_2)3$, $SiPh_2$, $Si(biphenyl)_1$, $Si(biphenyl)_2$, $Si(o-tolyl)_2$, more preferably $R^{10}$ is $SiMe_2$ or $SiPh_2$;
each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring;
c is an integer=0, 1, or 2;
d is an integer=0, 1, or 2;
e is an integer=0, 1, or 2;
The sum of c, d, and e is 1, 2 or 3, preferably the sum of c, d, and e is 1 or 2, more preferably, the sum of c, d, and e is 1;
provided that if the two $R^1$ groups are linked, then they do not form a butadiene group when M is Zr.

In an alternate embodiment, when M is Hf at least one $R^2$ group attached to a six carbon ring is not methyl, preferably at least two $R^2$ groups are not methyl, preferably at three $R^2$ groups are not methyl, preferably all four $R^2$ groups attached to a six carbon ring are not methyl.

In another preferred embodiment, M is Hf, and both $R^1$ groups are methyl.

In a preferred embodiment, the catalyst compounds used herein are represented by the Formula 3:

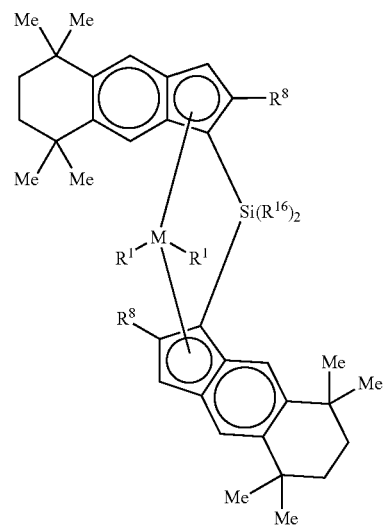

where:
M is a transition metal selected from group 4 of the periodic table, preferably Zr or Hf, most preferably Hf;
each $R^1$ is independently selected from the group consisting of hydrogen, hydrocarbyl, substituted hydrocarbyl and a functional group, preferably $R^1$ is a hydrogen, a hydrocarbon or a halide, more preferably $R^1$ is a hydride, methyl, ethyl, trimethylsilylmethyl, trimethylsilyl, phenyl, naphthyl, allyl, or benzyl, even more preferably $R^1$ is methyl, and the two $R^1$ groups may be the same or different, and the two $R^1$ groups may be linked, provided that if the two $R^1$ groups are linked, then they do not form a butadiene group when M is Zr;
Me is methyl;
each $R^8$ is independently selected from the group consisting of hydrogen, hydrocarbyl, substituted hydrocarbyl and a functional group, preferably $R^8$ is hydrogen, methyl, ethyl or propyl, more preferably $R^8$ is hydrogen or methyl, and the $R^8$ groups may be the same or different; and
each $R^{16}$ may be the same or different and the $R^{16}$ groups may be linked together to form a ring, preferably each $R^{16}$ is independently a methyl, ethyl, phenyl, biphenyl, o-tolyl, or an arene, preferably $R^{16}$ is methyl, ethyl, phenyl or an arene.

In any a preferred embodiment of any of the above formulae $R^8$ is not a phenyl group and or a substituted phenyl group.

In another preferred embodiment, if the two $R^1$ groups are linked, then they do not form a butadiene group when M is Ti.

In another preferred embodiment, if the two $R^1$ groups are linked, then they do not form a butadiene group when M is Hf.

In a preferred embodiment, the catalyst compounds used herein are represented by the following Formulae:

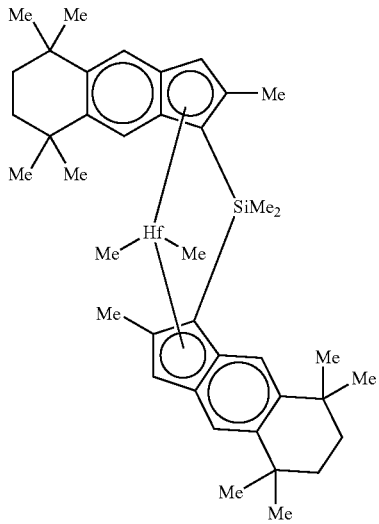

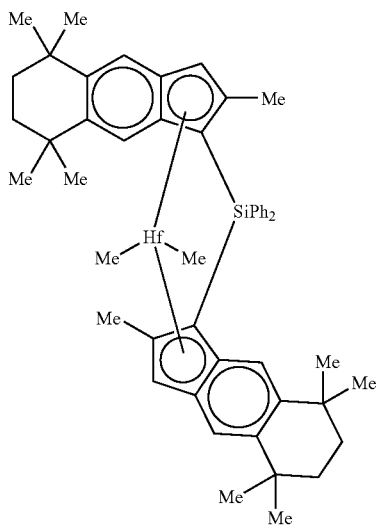

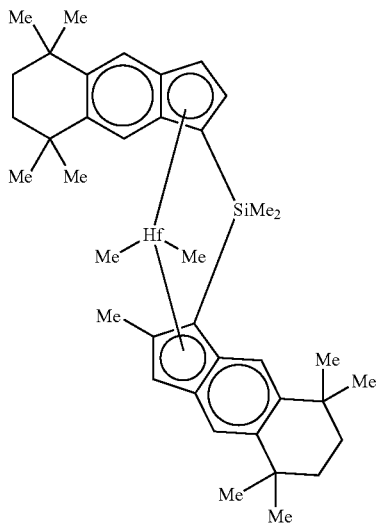

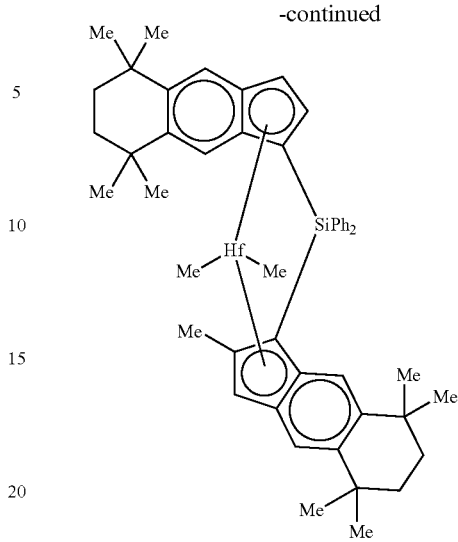

where Me is methyl, Hf is hafnium, Ph is phenyl, and Si is silicon.

In another embodiment, the catalysts compounds of this invention are present in a formal +4 oxidation state. In another embodiment, the catalysts compounds of this invention are not present in a formal +2 oxidation state. The nomenclature of formal oxidation states used here are described in length in the texts: Hegedus, L. S. Transition Metals in the Synthesis of Complex Organic Molecules 2nd Ed, University Science Press, 1999, Sausalito, Calif. and Collman, J. P. et. al. Principles and Applications of Organotransition Metal Chemistry. University Science Press, 1987, Sausalito, Calif.

In another preferred embodiment the catalyst compounds described herein may be used in combination with other polymerization and or oligomerization catalysts. In a preferred embodiment the instant catalyst compounds are used in combination with catalyst compounds described in any of the following references and references therein:

Hlatky, G. G. Chem. Rev. 2000, 100, 1347; Alt, H.; Koppl, A. Chem. Rev. 2000, 100, 1205; Resconi, L.; Cavallo, L.; Fait, A.; Piermontesi, F. Chem. Rev. 2000, 100, 1253; Bryntzinger, H. H.; et. al. Angew. Chem. Int. Ed. Engl. 1995, 34, 1143; Ittel, S. D.; Johnson, L. K.; Brookhart, M. Chem. Rev. 2000, 100, 1169; Gibson, V. C.; Spitzmesser, S. K. Chem. Rev. 2003, 103, 283.; Skupinska, J. Chem. Rev. 1991, 91, 613; Carter, A. et. al. Chem. Commun. 2002, 858; McGuinness, D. S.; et. al. J. Am. Chem. Soc. 2003, 125, 5272; McGuiness, D. S. Chem. Commun. 2003, 334.

Activators and Activation Methods for Catalyst Compounds

The bridged metallocene compounds according to this invention may be activated for polymerization catalysis in any manner sufficient to allow coordination or cationic polymerization. This can be achieved for coordination polymerization when one ligand can be abstracted and another will either allow insertion of the unsaturated monomers or will be similarly abstractable for replacement with a ligand that allows insertion of the unsaturated monomer (labile ligands), eg. alkyl, silyl or hydride. The traditional activators of coordination polymerization art are suitable, those typically include Lewis acids such as alumoxane compounds, and ionizing, anion precursor compounds that abstract one so as to ionize the bridged metallocene metal center in to a cation and provide a counterbalancing noncoordianting ion.

Alkylalumoxanes and modified alkylalumoxane are suitable as catalyst activators, particularly for the invention metal compounds where $R^1$=halide or other functional group. Alkylalumoxanes and modified alkylalumoxane are also suitable as catalyst for the invention metal compounds where $R^1$=hydrocarbyl or substituted hydrocarbyl. In one embodiment, one or more alumoxanes are utilized as an activator in the catalyst composition of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator at a 5000-fold molar excess Al/M over the catalyst precursor (per metal catalytic site). The minimum activator-to-catalyst-precursor is typically a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

It is within the scope of this invention to use an ionizing or stoichiometric activator, neutral or ionic, such as tri (n-butyl) ammonium tetrakis (pentafluorophenyl)boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, now abandoned, all of which are herein fully incorporated by reference.

Preferred activators include a cation and an anion component, and may be represented by the following formula:

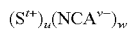

$S^{t+}$ is a cation component having the charge t+
$NCA^{v-}$ is a non-coordinating anion having the charge v−
t is an integer from 1 to 3.
v is an integer from 1 to 3.
u and v are constrained by the relationship: (u)x(t)=(v)x(w).

The cation component, ($S^{t+}$) may include Bronsted acids such as protons or protonated Lewis bases or reducible Lewis acids capable of protonating or abstracting a moiety, such as an akyl or aryl, from an analogous metallocene or Group 15 containing transition metal catalyst precursor, resulting in a cationic transition metal species.

In a preferred embodiment, the activators include a cation and an anion component, and may be represented by the following formula:

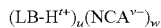

wherein LB is a neutral Lewis base;
H is hydrogen;
$NCA^{v-}$ is a non-coordinating anion having the charge v−
t is an integer from 1 to 3,
v is an integer from 1 to 3,
u and v are constrained by the relationship: (u)x(t)=(v)x(w).

The activating cation ($S^{t+}$) may be a Bronsted acid, (LB-$H^{t+}$), capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

The activating cation ($S^{t+}$) may also be an abstracting moiety such as silver, carboniums, tropylium, carbeniums, ferroceniums and mixtures, preferably carboniums and ferroceniums. Most preferably (S'+) is triphenyl carbonium or N,N-dimethylanilinium.

The anion component (NCA'−) includes those having the formula $[T^{x+}Qy]^{y-}$ wherein x is an integer from 1 to 3; y is an integer from 2 to 6; y−x v; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable (NCA'−) also include diboron compounds as disclosed in U.S. Pat. No. 5,447,895, which is fully incorporated herein by reference. Another example of a suitable anion is a borate with three ortho-substituted fluoroaryl ligands and one alkyne ligand. Another example of a suitable anion is a borate containing fluoroaryl groups with polar substitutents such as amines, ethers, silyl groups and derivatives thereof.

Additional suitable anions are known in the art and will be suitable for use with the catalysts of the invention. See in particular, patents U.S. Pat. No. 5,278,119, WO2002102857, WO2002051884, WO200218452, WO2000037513, WO2000029454, WO2000004058, WO9964476, WO2003049856, WO2003051892, WO2003040070, WO2003000740, WO2002036639, WO2002000738, WO2002000666, WO2001081435, WO2001042249, WO2000004059. Also see the review articles by S. H. Strauss, "The Search for Larger and More Weakly Coordinating Anions", *Chem. Rev.*, 93, 927-942 (1993) and C. A. Reed, "Carboranes: A New Class of Weakly Coordinating Anions for Strong Electrophiles, Oxidants and Superacids", *Acc. Chem. Res.*, 31, 133-139 (1998).

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis(heptafluoronaphthyl)borate, triethylammonium tetrakis(heptafluoronaphthyl)borate, tripropylammonium tetrakis(heptafluoronaphthyl)borate, tri (n-butyl)ammonium tetrakis(heptafluoronaphthyl)borate, tri (sec-butyl)ammonium tetrakis(heptafluoronaphthyl)borate, N,N-dimethylanilinium tetrakis(heptafluoronaphthyl)borate, N,N-diethylanilinium tetrakis(heptafluoronaphthyl)borate, trimethylammonium(2-perfluorobiphenyl)$_3$(perfluorophenylalkynyl)borate, triethylammonium(2-perfluorobiphenyl)$_3$ (perfluorophenylalkynyl)borate, tripropylammonium(2-perfluorobiphenyl)$_3$(perfluorophenylalkynyl)borate, tri(n-butyl) ammonium(2-perfluorobiphenyl)$_3$(perfluorophenylalkynyl) borate, tri(sec-butyl)ammonium(2-perfluorobiphenyl)$_3$ (perfluorophenylalkynyl)borate, N,N-dimethylanilinium(2-perfluorobiphenyl)$_3$(perfluorophenylalkynyl)borate, N,N-diethylanilinium(2-perfluorobiphenyl)$_3$ (perfluorophenylalkynyl)borate, trimethylammonium tetrakis-(2,3,4,6-tetrafluorophenylborate, triethylammonium tetrakis-(2,3,4,6-tetrafluorophenyl)borate, tripropylammonium tetrakis-(2,3,4,6-tetrafluorophenyl) borate, tri(n-butyl) ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3, 4,6-tetrafluoro-phenyl)borate, and N,N-dimethyl-(2,4,6-trimethylanilinium)tetrakis-(2,3,4,6-tetrafluorophenyl) borate; dialkyl ammonium salts such as: di-(i-propyl) ammonium tetrakis(pentafluorophenyl) borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl) borate; non-Bronsted acids such as triphenylcarbenium tetrakis(pentafluorophenyl)borate, triphenylcarbenium tetrakis(heptafluoronaphthyl)borate, triphenylcarbenium (2-perfluorobiphenyl)$_3$(Perfluorophenylalkynyl)borate, trisperfluorophenyl borane, and triperfluoronaphthyl borane.

Most preferably, the ionic stoichiometric activator is N,N-dimethylanilinium tetrakis(perfluorophenyl)borate and/or triphenylcarbenium tetrakis(perfluorophenyl)borate.

In one embodiment, activation methods using ionizing ionic compounds not containing an active proton but capable of producing an analogous metallocene catalyst cation and their non-coordinating anion are also contemplated and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When $R^1$ is a functional group ligand, such as chloride, amido or alkoxy ligands, and the functional group ligands are not capable of discrete ionizing abstraction with the ionizing, anion pre-cursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with analogous dihalide substituted metallocene compounds prior to or with the addition of activating noncoordinating anion precursor compounds.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

In general the combined metal compounds and the activator are combined in ratios of about 1000:1 to about 0.5:1. In a preferred embodiment the metal compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

In a preferred embodiment the ratio of the first catalyst to the second or additional catalyst is 5:95 to 95:5, preferably 25:75 to 75:25, even more preferably 40:60 to 60:40.

In another embodiment the activator used herein is not an alumoxane. Alternately the catalyst system used herein comprises les than 0.1 weight % of an alumoxane.

In another embodiment the catalyst compositions of this invention include a support material or carrier. For example, the one or more catalyst components and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

Preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

Monomers

In a preferred embodiment the transition metal compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methyl-pentene-1, 3-methyl pentene-1, 3,5,5-trimethyl hexene 1, and 5-ethyl-1-nonene.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also useful herein. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include 6-nitro-1-hexene, N-methylallylamine, N-allylcyclopentylamine, N-allylhexylamine, methyl vinyl ketone, ethyl vinyl ketone, 5-hexen-2-one, 2-acetyl-5-norbornene, 7-syn methoxymethyl-5-norbornen-2-one, acrolein, 2,2-dimethyl-4-pentenal, undecylenic aldehyde, 2,4-dimethyl-2,6-heptadienal, acrylic acid, vinylacetic acid, 4-pentenoic acid, 2,2-dimethyl-4-pentenoic acid, 6-heptenoic acid, trans-2,4-pentadienoic acid, 2,6-heptadienoic acid, nona-fluoro-1-hexene, allyl alcohol, 7-octene-1,2-diol, 2-methyl-3-buten-1-ol, 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$] octasiloxane, 2-benzoyl-5-norbornene, allyl 1,1,2,2,-tetrafluoroethyl ether, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopentene-1-one ethylene ketal, allyl disulfide, ethyl acrylate, methyl acrylate. It is recognized to one skilled in the art that the use of polar monomers in polymerization processes require the use of Lewis-acid cocatalysts, such as alkyl aluminum compounds, or an alternative protection method to effect polymerization (Boffa, L. S.; Novak, B. M. *Chem. Rev.* 2000, 1479 and references therein).

For purposes of this invention and the claims thereto, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

Polymerization Processes

A preferred polymerization is a single stage, steady state, polymerization conducted in a well-mixed continuous feed polymerization reactor. The polymerization can be conducted in solution, although other polymerization procedures such as gas phase or slurry polymerization, which fulfill the requirements of single stage polymerization and continuous feed reactors, can also be used. The process can be described as a continuous, non-batch process that, in its steady state operation, is exemplified by removal of amounts of polymer made per unit time, being substantially equal to the amount of polymer withdrawn from the reaction vessel per unit time. By "substantially equal" we intend that these amounts, polymer made per unit time, and polymer withdrawn per unit time, are in ratios of one to other, of from 0.9:1; or 0.95:1; or 0.97:1; or 1:1. In such a reactor, there is preferably a substantially homogeneous monomer distribution. At the same time, the polymerization is accomplished in substantially single step or stage or in a single reactor, as contrasted to multistage or multiple reactors (two or more). Multiple reactors where each of the above of reactors is of this description are also useful herein.

A preferred method of making polymer using the polymerization catalysts described herein comprise the following steps: a) feeding solvent and a set of monomers in predetermined proportions to a polymerization reactor, b) adding a soluble metallocene catalyst to said reactor, c) polymerizing the set of monomers in solution to produce an effluent containing a polymer wherein the first and second set of monomers are chosen from the group propylene, ethylene, alpha-olefin, non-conjugated diene. Likewise Polymers may be made by solution polymerization in a train of at least two continuous flow stirred tank reactors (CFSTR) connected in series with the addition of a metallocene catalyst. Each reactor should be capable of being fed independently with monomer and solvent. In order to remove polar compounds that act as catalyst poisons, all solvent and monomer feeds are desirably purified over mole sieves, alumina beds, or other absorbents as known in the art. Heat removal from the reactor is by methods well known in the art such as auto-refrigeration, feed prechilling (adiabatic reactors), cooling coils, or various combinations of these techniques. Adiabatic reactors with prechilled feeds are preferred. Pressure is preferably sufficient to keep the reactor contents in solution at the reactor temperature. Polymerization may be carried out at temperatures in the range of −20° C. or lower to 200° C. or higher, and preferably, at 0° C. to 160° C. Most preferably polymerization is conducted in a range of 55° C. to 140° C. The residence time per reactor is maintained at 1 to 180 minutes and preferably at 5 to 30 minutes. The polymer concentration in the effluent of the reactors is maintained in the range of 1 to 20% by weight and more preferably between 3 to 12% by weight. The overall polymerization rate is set by the catalyst and monomer feed rates. Polymer composition is controlled by adjusting the monomer feed rate to a reactor. Polymer molecular weight is set by choosing the reactor temperature, (MW decreases with temperature increases), monomer concentration (MW increases with increasing monomer concentration), and by optionally adding chain transfer agents such as hydrogen. The polymer product can be conventionally recovered from the effluent by coagulation with a nonsolvent such as isopropyl alcohol, acetone, or n-butyl alcohol, or the polymer can be recovered by stripping the solvent or other media with heat or steam. One or more conventional additives such as antioxidants can be incorporated in the polymer during the recovery procedure. Useful antioxidants include phenyl-beta-naphthylamine, di-tert-butylhydroquinone, triphenyl phosphate, heptylated diphenylamine, 2,2'-methylene-bis(4-methyl-6-tert-butyl)phenol, and 2,2,4-trimethyl-6-phenyl-1,2-dihydroquinoline.

Polymerization may be conducted by any of the polymerization procedures known in the art, however, in a preferred embodiment the polymerization is conducted in a solution polymerization under conditions where the components are completely in solution. These polymerization conditions are obtained by the choice of a solvent, in sufficient quantity, common to both of the polymeric components as the polymerization medium at suitable reaction conditions, including temperature and pressure, such that all of the components of the polymer mixture are maintained in solution. Solvents useful in this invention include hydrocarbons such as aliphatics, cycloalphatics, and aromatic hydrocarbons. Preferred solvents are C12 or lower straight-chain or branched-chain, saturated hydrocarbons, and C5 to C9 saturated alicyclic or aromatic hydrocarbons. Examples of such solvents or reaction media are hexane, butane, pentane, heptane, cyclopentane, cyclohexane, cycloheptane, methyl cyclopentane, methyl cyclohexane, isooctane, benzene, toluene, xylene, with hexane being preferred.

Typically one or more transition metal compounds, one or more activators, and one or more monomers are contacted to produce polymer. The components may be contacted in a solution, bulk, gas or slurry polymerization process or a combination thereof, preferably solution phase or bulk phase polymerization process.

In general the transition metal compound and the activator are combined in ratios of about 1:10,000 to about 1:1, in other embodiments the combined transition metal compounds and the activator are combined in ratios of 1:1 to 100:1. When alumoxane or aluminum alkyl activators are used, the combined pre-catalyst-to-activator molar ratio is from 1:5000 to 10:1, alternatively from 1:1000 to 10:1; alternatively, 1:500 to 2:1; or 1:300 to 1:1. When ionizing activators are used, the combined pre-catalyst-to-activator molar ratio is from 10:1 to 1:10; 5:1 to 1:5; 2:1 to 1:2; or 1.2:1 to 1:1. Multiple activators maybe used, including using mixtures of alumoxanes or aluminum alkyls with ionizing activators.

One or more reactors in series or in parallel may be used in the present invention. Catalyst component and activator may be delivered as a solution or slurry, either separately to the reactor, activated in-line just prior to the reactor, or preactivated and pumped as an activated solution or slurry to the reactor. A preferred operation is two solutions activated in-line. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

Ethylene-alpha-olefin (including ethylene-cyclic olefin and ethylene-alpha-olefin-diolefin) polymers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

Gas Phase Polymerization

The catalyst compounds described herein may be used in gas phase polymerization processes. Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.) The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kpa) to about 400 psig (2759 kPa), more preferably in the range of from about 250 psig (1724 kPa) to about 350 psig (2414 kPa). The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455

Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr ( 45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

The catalyst compounds described herein may be used in slurry phase polymerization processes. A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique useful in the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

Homogeneous or Solution Phase Polymerization

The catalysts described herein can be used advantageously in homogeneous and or solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling and the monomer feed my or may not be refrigerated. See the general disclosure of U.S. Pat. No. 5,001,205 for general process conditions. See also, international application WO 96/33227 and WO 97/22639.

In a particularly preferred embodiment, a continuous solution polymerization process is used with the catalyst compounds of this invention (preferably one or more of dimethylsilyl bis(2-(methyl)-5,5,8,8-tetramethyl-5,6,7,8-tetrahydrobenz(f)indenyl)hafnium dimethyl, diphenylsilyl bis(2-(methyl)-5,5,8,8-tetramethyl-5,6,7,8-tetrahydrobenz(f)indenyl)hafnium dimethyl, diphenylsilyl bis(5,5,8,8-tetramethyl-5,6,7,8-tetrahydrobenz(f)indenyl)hafnium dimethyl, diphenylsilyl bis(2-(methyl)-5,5,8,8-tetramethyl-5,6,7,8-tetrahydrobenz(f)indenyl)zirconium dichloride, and cyclo-propylsilyl bis(2-(methyl)-5,5,8,8-tetramethyl-5,6,7,8-tetrahydrobenz(f)indenyl)hafnium dimethyl.) to produce copolymers of ethylene/octene or ethylene/propylene or terpolymers of ethylene/propylene/diene, preferably copolymers of propylene and from 1 to 20 weight % ethylene. (By continuous is meant a system that operates (or is intended to operate) without interruption or cessation. For example a continuous process to produce a polymer would be one where the reactants are continually introduced into one or more reactors and polymer product is continually withdrawn.) An organoaluminum compound, namely, tri-n-octylaluminum, may be added as a scavenger to the monomer feed streams prior to introduction into the polymerization process. For production of more crystalline polymers, the catalyst is preferably used in combination with dimethylaniliniumtetrakis (pentafluorophenyl)borate. Preferably the solution polymerization is conducted in a single, or optionally in two, continuous stirred tank reactors connected in series with hexane used as the solvent. In addition, toluene may be added to increase the solubility of the co-catalyst. The feed is transferred to the first reactor where the exothermic polymerization reaction is conducted adiabatically at a reaction temperature between about 50° C. to about 220° C. Hydrogen gas may also be added to the reactors as a further molecular weight regulator. If desired, polymer product is then transferred to the second reactor, which is also operated adiabatically at a temperature between about 50° C. to 200° C. Additional monomers, solvent, metallocene catalyst, and activators can be fed to the second reactor. The polymer content leaving the second reactor is preferably from 8 to 22 weight percent. A heat exchanger then heats the polymer solution to a temperature of about 220° C. The polymer solution is then brought to a Lower Critical Solution Temperature (LCST) liquid-liquid phase separator which causes the polymer solution to separate into two liquid phases—an upper lean phase and a lower polymer-rich phase. The upper lean phase contains about 70 wt. % of the solvent and the lower polymer rich phase contains about 30 wt. % polymer. The polymer solution then enters a low pressure separator vessel which operates at a temperature of about 150° C. and a pressure of 4-10 barg (400 to 1000 Pa) and flashes the lower polymer rich phase to remove volatiles and to increase the polymer content to about 76 wt. %. A gear pump at the bottom of the flash vessel drives the polymer rich solution to a List devolatilizer. An extruder is coupled to the end of the List devolatizer whereby the polymer material is transferred to a gear pump which pushes the polymer material through a screen pack. Then the polymer is cut into pellets and fed to a water bath. A spin dryer dries the polymer pellets which have a final solvent content of less than about 0.5 wt. %.

In a preferred embodiment, the monomer (preferably propylene) is present in the feed into the reactor at 50 weight % or less, preferably between 5 and 40 weight%, preferably 5 and 30 weight %, preferably between 5 and 25 weight %, based upon the weight of the feed. Preferably the monomer is combined with a solvent (such as butane, isobutene, pentane, hexane, octane or the like, preferably hexane) just prior to entry into the reactor. In a preferred embodiment, the catalyst system converts at least 20% of the monomer to polymer, preferably at least 30%, preferably at least 35%, preferably at least 40%, preferably at least 50%, based upon the weight of the monomer introduced into the reactor. In a preferred embodiment, the catalyst system converts at least 20% of the propylene to polypropylene, preferably at least 30%, preferably at least 35%, preferably at least 40%, preferably at least 50%, based upon the weight of the propylene introduced into the reactor.

Polymers

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the copolymers comprises one or more diolefin comonomers, preferably one or more $C_2$ to $C_{40}$ diolefins.

Other olefinically unsaturated monomers besides those specifically described above may be polymerized using the catalysts according to the invention, for example, styrene, alkyl-substituted styrenes, isobutylene and other geminally disubstituted olefins, ethylidene norbornene, norbornadiene, dicyclopentadiene, and other olefinically-unsaturated monomers, including other cyclic olefins, such as cyclopentene, norbornene, alkyl-substituted norbornenes, and vinyl group-containing polar monomers capable of coordination polymerization. See, for example, U.S. Pat. Nos. 5,635,573, 5,763,556, and WO 99/30822. Additionally, alpha-olefinic macromonomers of up to 1000 mer units, or more, may also be incorporated by copolymerization yielding branch-containing olefin polymers.

Ethylene Polymers

Linear polyethylene, including high and ultra-high molecular weight polyethylenes, including both homo- and copolymers with other alpha-olefin monomers, alpha-olefinic and/or non-conjugated diolefins, for example, $C_3$-$C_{20}$ olefins, diolefins or cyclic olefins, can be produced by adding ethylene, and optionally one or more of the other monomers, to a reaction vessel under low pressure (typically <50 bar), at a typical temperature of 40-250° C. with the invention catalyst that has been slurried with a solvent, such as hexane or toluene. Heat of polymerization is typically removed by cooling. Gas phase polymerization can be conducted, for example, in a continuous fluid bed gas-phase reactor operated at 2000-3000 kPa and 60-160° C., using hydrogen as a reaction modifier (100-200 PPM), $C_4$-$C_8$ comonomer feedstream (0.5-1.2 mol %), and $C_2$ feedstream (25-35 mol %). See, U.S. Pat. Nos. 4,543,399, 4,588,790, 5,028,670 and 5,405,922 and 5,462,999, which are incorporated by reference for purposes of U.S. patent practice.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methyl-pentene-1, 3-methyl pentene-1, and 3,5,5-trimethyl hexene 1.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the a-olefin or cyclic olefin or mixture thereof with other monomers, polymerizable and not, as a polymerization diluent in which the invention catalyst is suspended. Typical ethylene pressures will be between 10 and 1000 psig (69-6895 kPa) and the polymerization diluent temperature will typically be between 40 and 160° C. The process can be carried out in a stirred tank reactor, or more than one operated in series or parallel. See the general disclosure of U.S. Pat. No. 5,001,205 for general process conditions. See also, International Applications WO 96/33227 and WO 97/22639. All documents are incorporated by reference for description of polymerization processes, metallocene selection and useful scavenging compounds.

Propylene Copolymers

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methyl-pentene-1, 3-methyl pentene-1, and 3,5,5-trimethyl hexene 1.

In another preferred embodiment the polymer produced herein is a copolymer of propylene and ethylene and optionally one or more $C_4$ to $C_{20}$ linear, branched or cyclic monomers, preferably one or more $C_2$ or $C_4$ to $C_{12}$ linear, branched or cyclic alpha-olefins.

In another preferred embodiment the polymer produced herein is a copolymer of propylene and ethylene the copolymer includes from a lower limit of 3% or 5% or 6% or 8% or 10% by weight to an upper limit of 20% or 25% by weight ethylene derived units, and from a lower limit of 75% or 80% by weight to an upper limit of 95% or 94% or 92% or 90% by weight propylene-derived units, the percentages by weight based on the total weight of propylene- and ethylene-derived units. Within these ranges, these copolymers are mildly crystalline as measured by differential scanning calorimetry (DSC), and are exceptionally soft, while still retaining substantial tensile strength and elasticity. At ethylene compositions lower than the above limits for the copolymer, such polymers are generally crystalline, similar to crystalline isotactic polypropylene, and while having excellent tensile strength, they do not have the favorable softness and elasticity. At ethylene compositions higher than the above limits for the copolymer component, the copolymer is substantially amorphous. The ethylene composition of a polymer is measured as follows. A thin homogeneous film is pressed at a temperature of about 150° C. or greater, then mounted on a Perkin Elmer PE 1760 infrared spectrophotometer. A full spectrum of the sample from 600 $cm^{-1}$ to 4000 $cm^{-1}$ is recorded and the monomer weight percent of ethylene can be calculated according to the following equation: Ethylene wt %=82.585−111.987X+30.045 $X^2$, wherein X is the ratio of the peak height at 1155 $cm^{-1}$ and peak height at either 722 $cm^{-1}$ or 732 $cm^{-1}$, whichever is higher.

In one embodiment, the polymer is a random propylene copolymer having a narrow compositional distribution. The copolymer is described as random because for a polymer comprising propylene, comonomer, and optionally diene, the number and distribution of comonomer residues is consistent with the random statistical polymerization of the monomers. In stereoblock structures, the number of block monomer residues of any one kind adjacent to one another is greater than predicted from a statistical distribution in random copolymers with a similar composition. Historical ethylene-propylene copolymers with stereoblock structure have a distribution of ethylene residues consistent with these blocky structures rather than a random statistical distribution of the monomer residues in the polymer.

In various embodiments, features of the copolymers include some or all of the following characteristics, where ranges from any recited upper limit to any recited lower limit are contemplated:

(i) a melting point ranging from an upper limit of less than 110° C., or less than 90° C., or less than 80° C., or less than 70° C., to a lower limit of greater than 25° C., or greater than 35° C., or greater than 40° C., or greater than 45° C.;

(ii) a heat of fusion ranging from a lower limit of greater than 1.0 joule per gram (J/g), or greater than 1.5 J/g, or greater than 4.0 J/g, or greater than 6.0 J/g, or greater than 7.0 J/g, to an upper limit of less than 125 J/g, or less than 100 J/g, or less than 75 J/g, or less than 60 J/g, or less than 50 J/g, or less than 40 J/g, or less than 30 J/g;

(iii) a triad tacticity as determined by carbon-13 nuclear magnetic resonance (C13 NMR) of greater than 75%, or greater than 80%, or greater than 85%, or greater than 90%;

(iv) a tacticity index m/r ranging from a lower limit of 4 or 6 to an 5 upper limit of 8 or 10 or 12;

(v) an intermolecular tacticity such that at least X % by weight of the copolymer is soluble in two adjacent temperature fractions of a thermal fractionation carried out in hexane in 8° C. increments, where X is 75, or 80, or 85 or 90, or 95, or 97, or 99;

(vi) a reactivity ratio product $r_1r_2$ of less than 1.5, or less than 1.3, or less than 1.0, or less than 0. 8;

(vii) a molecular weight distribution Mw/Mn ranging from a lower limit of 1.5 or 1.8 to an upper limit of 40 or 20 or 10 or 5 or 3;

(viii) a molecular weight of from 15,000-5,000,000;

(ix) an elasticity as defined herein of less than 30%, or less than 20%, or less than 10%, or less than 8%, or less than 5%; and or (x) a 500% tensile modulus of greater than 0.5 MPa, or greater than 0.8 MPa, or greater than 1.0 MPa, or greater than 2. 0 MPa.

Melting Point, Percent Crystallinity and Heat of Fusion

Melting point (second melt), percent crystallinity and heat of fusion are determined according to the following DSC procedure: Differential scanning calorimetric (DSC) trace data is obtained using a TA Instruments model 2920 machine. Samples weighing approximately 7-10 mg are sealed in aluminum sample pans. The DSC data are recorded by first cooling the sample to −50° C. and then gradually heating it to 200° C. at a rate of 10° C./minute. The sample is kept at 200° C. for 5 minutes before a second cooling-heating cycle is applied. Both the first and second cycle thermal events are recorded. Areas under the melting curves are measured and used to determine the heat of fusion and the degree of crystallinity. The percent crystallinity is calculated using the formula, [area under the curve (Joules/gram)/B (Joules/gram)]*100, where B is the heat of fusion for the homopolymer of the major monomer component. These values for B are to be obtained from the Polymer Handbook, Fourth Edition, published by John Wiley and Sons, New York 1999. A value of 189 J/g (B) is used as the heat of fusion for polypropylene.

Triad Tacticity

An ancillary procedure for the description of the tacticity of the propylene units of embodiments of the current invention is the use of triad tacticity. The triad tacticity of a polymer is the relative tacticity of a sequence of three adjacent propylene units, a chain consisting of head to tail bonds, expressed as a binary combination of m and r sequences. It is usually expressed for copolymers of the present invention as the ratio of the number of units of the specified tacticity to all of the propylene triads in the copolymer.

The mm triad tacticity (mm fraction) of a propylene copolymer can be determined from a $^{13}C$ NMR spectrum of the propylene copolymer and the following formula:

$$mm\ \text{Fraction} = \frac{PPP(mm)}{PPP(mm) + PPP(mr) + PPP(rr)}$$

where PPP(mm), PPP(mr) and PPP(rr) denote peak areas derived from the methyl groups of the second units in the following three propylene unit chains consisting of head-to-tail bonds:

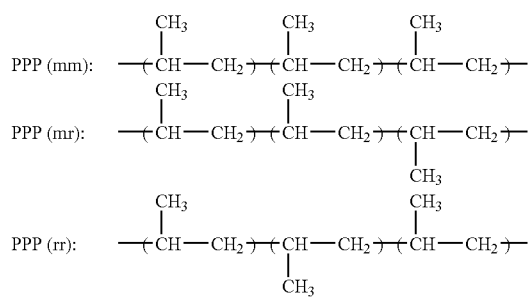

The 13C NMR spectrum of the propylene copolymer is measured and the triad tacticity determined as described in U.S. Pat. No. 5,504,172 and references therein. The propylene copolymers of embodiments of our invention have an mm triad tacticity of three propylene units, as measured by 13C NMR, of greater than 75%, or greater than 80%, or greater than 82%, or greater than 85%, or greater than 90%.

Tacticity Index

The tacticity index, expressed herein as "m/r", is determined by $^{13}C$ nuclear magnetic resonance (NMR). The tacticity index m/r is calculated as defined in H. N. Cheng, Macromolecules, 17, 1950 (1984). The designation "m" or "r" describes the stereochemistry of pairs of contiguous propylene groups, "m" referring to meso and "r" to racemic. An m/r ratio of 1.0 generally describes a syndiotactic polymer, and an m/r ratio of 2.0 an atactic material. An isotactic material theoretically may have a ratio approaching infinity, and many by-product atactic polymers have sufficient isotactic content to result in ratios of greater than 50. Copolymers of embodiments of our invention can have a tacticity index m/r ranging from a lower limit of 4 or 6 to an upper limit of 8 or 12.

Intermolecular Tacticity

Molecular Structure: Homogeneous Distribution:

Homogeneous distribution is defined as a statistically insignificant intermolecular difference of both in the composition of the copolymer and in the tacticity of the polymerized propylene. For a copolymer to have a homogeneous distribution it must meet the requirement of two independent tests: (i) intermolecular distribution of tacticity; and (ii) intermolecular distribution of composition, which are described below. These tests are a measure of the statistically insignificant intermolecular differences of tacticity of the polymerized propylene and the composition of the copolymer, respectively.

Intermolecular Distribution of Tacticity:

Preferred polymer produced herein have a statistically insignificant intermolecular difference of tacticity of polymerized propylene between different chains (intermolecularly.). This is determined by thermal fractionation by controlled dissolution generally in a single solvent, at a series of slowly elevated temperatures. A typical solvent is a saturated hydrocarbon such as hexane or heptane. These controlled dissolution procedures are commonly used to separate similar polymers of different crystallinity due to differences in isotactic propylene sequences, as shown in the article in *Macromolecules*, Vol. 26, p2064 (1993).

In embodiments of our invention, at least 75% by weight, or at least 80% by weight, or at least 85% by weight, or at least 90% by weight, or at least 95% by weight, or at least 97% by weight, or at least 99% by weight of the polymer is soluble in a single temperature fraction, or in two adjacent temperature fractions, with the balance of the polymer in immediately preceding or succeeding temperature fractions. These percentages are fractions, for instance in hexane, beginning at 23° C. and the subsequent fractions are in approximately 8° C. increments above 23° C. Meeting such a fractionation requirement means that a polymer has statistically insignificant intermolecular differences of tacticity of the polymerized propylene.

Intermolecular Distribution of Composition:

Preferred polymers produced herein have statistically insignificant intermolecular differences of composition, which is the ratio of propylene to ethylene between different chains (intermolecular). This compositional analysis is by infrared spectroscopy of the fractions of the polymer obtained by the controlled thermal dissolution procedure described above.

A measure of the statistically insignificant intermolecular differences of composition, each of these fractions has a composition (wt. % ethylene content) with a difference of less than 1.5 wt. % (absolute) or less than 1.0 wt. % (absolute), or less than 0.8 wt. % (absolute) of the average wt. % ethylene content of the whole polymer. Meeting such a fractionation requirement means that a polymer has statistically insignificant intermolecular differences of composition, which is the ratio of propylene to comonomer (such as ethylene).

To produce a copolymer having the desired randomness and narrow composition, it is beneficial if (1) a single sited metallocene catalyst is used which allows only a single statistical mode of addition of the first and second monomer sequences and (2) the copolymer is well-mixed in a continuous flow stirred tank polymerization reactor which allows only a single polymerization environment for substantially all of the polymer chains of the copolymer.

Molecular Weight and Molecular Weight Distribution

Mw, Mn, Mz and Mw/Mn are determined using an instrument containing columns packed with porous beads, an elution solvent, and detector in order to separate polymer molecules of different sizes. Molecular weights for ethylene propylene copolymers were measured by gel permeation chromatography using (1) an Alliance 2000 GPC3D equipped with differential refractive index (DRI) and viscometry detectors and an 18 angle light scattering detector or (2) a Polymer Labs 220 GPC 3D equipped with DRI, viscometry and an 3 angle light scattering detector. Detectors were calibrated using polystyrene standards Samples were run in 1,2,4-trichlorobenzene (135° C.) using three Polymer Laboratories PC Gel mixed B LS columns in series. A correlation of polystyrene retention volume obtained from the standards, to the retention volume of the polymer tested yields the polymer molecular weight.

Average molecular weights M can be computed from the expression:

$$M = \frac{\sum_i N_i M_i^{n+1}}{\sum_i N_i M_i^n}$$

where Ni is the number of molecules having a molecular weight Mi. When n=0, M is the number average molecular weight Mn. When n=1, M is the weight average molecular weight Mw. When n=2, M is the Z-average molecular weight Mz. The desired MWD function (e.g., Mw/Mn or Mz/Mw) is the ratio of the corresponding M values. Measurement of M and MWD is well known in the art and is discussed in more detail in, for example, Slade, P. E. Ed., *Polymer Molecular Weights Part II*, Marcel Dekker, Inc., NY, (1975) 287-368; Rodriguez, F., *Principles of Polymer Systems* 3rd ed., Hemisphere Pub. Corp., NY, (1989) 155-160; U.S. Pat. No. 4,540,753; Verstrate et al., *Macromolecules*, vol. 21, (1988) 3360; and references cited therein.

Preferred polymers produced herein have a weight average molecular weight (Mw) within the range having an upper limit of 5,000,000 g/mol, 1,000,000 g/mol, or 500,000 g/mol, and a lower limit of 10,000 g/mol, 20,000 g/mol, or 80,000 g/mol, and a molecular weight distribution Mw/Mn (MWD), sometimes referred to as a "polydispersity index" (PDI), ranging from a lower limit of 1.5, 1.8, or 2.0 to an upper limit of 40, 20, 10, 5, or 4.5.

In one embodiment, the polymers produced herein have a Mooney viscosity, ML(1+4)@125° C., of 100 or less, 75 or less, 60 or less, or 30 or less. Mooney viscosity, as used herein, can be measured as ML(1+4)@125° C. according to ASTM D1646, unless otherwise specified.

Elasticity

Elasticity is determined according to ASTM D 790 as described at column 17, line 19 to line 49 of U.S. Pat. No. 6,525,157.

Tensile Modulus

Tensile Modulus is determined according to ASTM D 638 at 20 inches per minute (51 cm/min) using dumbbell shapes as described at column 17, line 1 to 17 of U.S. Pat. No. 6,525,157.

Melt Index

In embodiments of the present invention, the polymers produced herein have a melt index (MI) of 20 dg/min or less, 7 dg/min or less, 5 dg/min or less, or 2 dg/min or less, or less than 2 dg/min. The determination of the melt index of the polymer is according to ASTM D1238 (230° C., 2.16 kg) Procedure A. In this version of the method a portion of the sample extruded during the test was collected and weighed. This is commonly referred to as the modification 1 of the experimental procedure. The sample analysis is conducted at 190° C. with a 1 minute preheat on the sample to provide a steady temperature for the duration of the experiment.

Stereo- and Regio-Errors in Insertion of Propylene: 2,1 and 1,3 Insertions

In polyolefins prepared by polymerization of α-olefins of three or more carbon atoms in the presence of a chiral metallocene catalyst, 2,1-insertion or 1,3-insertion takes place in addition to the usual 1,2-insertion, such that inversely inserted units such as a 2,1-insertion or a 1,3-insertion are formed in the olefin polymer molecule (see, *Macromolecular Chemistry Rapid Communication*, Volume 8, page 305 (1987), by K. Soga, T. Shiono, S. Takemura and W. Kaminski). Thus, the insertion of propylene can occur to a small extent by either 2,1 (tail to tail) or 1,3 insertions (end to end). The proportion of the 2,1-insertions to all of the propylene insertions in a propylene elastomer is calculated by the method described by Tsutsui, T. et. al. *Polymer*, 1989, 30, 1350. The extent of 1,3 insertions are determined according to the procedure described in U.S. Pat. No. 5,504,172. In a preferred embodiment, the proportion of inversely inserted propylene units of polymers produced herein, based on the 2,1-insertion of a propylene monomer in all propylene insertions, as measured by $^{13}C$ NMR, is greater than 0.5%, or greater than 0.6%. based on the 1,3-insertion of a propylene monomer, as measured by $^{13}C$ NMR, is greater than 0.05%, or greater than 0.06%, or greater than 0.07%, or greater than 0.08%, or greater than 0.085 percent.

In a preferred embodiment, the polymers produced herein are random copolymers of propylene and ethylene having a heat of fusion as determined by Differential Scanning Calorimetry (DSC) of less than 50 J/g, a melt index (MI) of less than 5 dg/min, and containing stereoregular propylene crystallinity. Preferably the polymer is a random copolymer of propylene and at least one comonomer selected from ethylene, $C_4$-$C_{12}$ α-olefins, and combinations thereof, preferably the polymer comprises from 2 wt % to 25 wt % polymerized ethylene units, based on the total weight of the polymer.

In another preferred embodiment, the polymer produced herein comprises:
- a first monomer present at from 40 to 95 mole %, preferably 50 to 90 mole %, preferably 60 to 80 mole %, and
- a comonomer present at from 5 to 40 mole %, preferably 10 to 60 mole %, more preferably 20 to 40 mole %, and
- a termonomer present at from 0 to 10 mole %, more preferably from 0.5 to 5 mole %, more preferably 1 to 3 mole %.

Preferably the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclohexene, cyclooctene, hexadiene, cyclohexadiene and the like. Preferably the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene. Preferably the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5, 5-trimethyl hexene-1, 3-methylpentene-1, 4-methylpentene-1, cyclopentadiene, and cyclohexene. In a preferred embodiment the copolymers described herein comprise at least 50 mole % of a first monomer and up to 50 mole % of other monomers.

In the measurement of properties ascribed to some polymers produced herein, there is preferably a substantial absence of a secondary or tertiary polymer or polymers to form a blend. By "substantial absence" we intend less than 10%, or 15 less than 5%, or less than 2.5%, or less than 1%, or 0%, by weight.

Blends

The catalyst compositions of the invention can be used as described above individually for coordination polymerization or can be mixed to prepare polymer blends with other known olefin polymerization catalyst compounds. By selection of monomers, blends of coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

It is generally believed that in situ blending provides a more homogeneous product and allows the blend to be produced in one step. The use of mixed catalyst systems for in situ blending involves combining more than one catalyst in the same reactor to simultaneously produce multiple distinct polymer products. This method requires additional catalyst synthesis and the various catalyst components must be matched for their activities, the polymer products they generate at specific conditions, and their response to changes in polymerization conditions. In a preferred embodiment, polymers produced herein can be thermoplastic polymer compositions composed of a majority of propylene with a minor amount of ethylene or other alpha olefins having between 4 to 20 carbon atoms. These polymer compositions include a linear, single homogeneous macromolecular copolymer structure. These polymers have limited crystallinity due to adjacent isotactic propylene units and have a melting point of between 25 and 110° C. They are preferably generally devoid of any substantial intermolecular heterogeneity in tacticity and comonomer composition. They are also devoid of any substantial heterogeneity in intramolecular composition distribution. In addition, these thermoplastic polymer compositions are soft and elastic.

In all previous embodiments including but not limited to ethylene polymers, ethylene copolymers, propylene polymers, other polymers and blends, the polymers described above may further comprise one or more dienes at up to 16 weight %, preferably at the lower limit of 0.00001 wt %, preferably at a lower limit of 0.002, preferably at a lower limit of 0.3 weight %, preferably to 0.5 weight %, even more preferably 0.75 wt % and to a higher limit of to 1.0 weight %, a higher limit of 3 wt % and a higher limit of 7 wt % and a higher limit of 15 wt % based upon the total weight of the composition. All of these percentages are by weight, based upon the weight of the copolymer. The presence or absence of diene can be conventionally determined by infrared techniques well known to those skilled in the art. Sources of diene include diene monomer added to the polymerization of ethylene and propylene, or use of diene in catalysts. Non-conjugated dienes useful as co-monomers are preferably straight chain, hydrocarbon di-olefins or cycloalkenyl-substituted alkenes, having 6 to 15 carbon atoms, for example: (a) straight chain acyclic dienes, such as 1,4-hexadiene and 1,6-octadiene; (b) branched chain acyclic dienes, such as 5-m ethyl-1,4-hexadi ene; 3,7-dimethyl-1,6-octadiene; 3,7-dimethyl-1,7-octadiene; and the mixed isomers of dihydro-myricene and dihydro-ocinene; (c) single ring alicyclic dienes, such as C ID 1,3-cyclopentadiene, 1,4-cyclohexadiene; 1,5-cyclo-octadiene and 1,5-cyclododecadiene; (d) multi-ring alicyclic fused and bridged ring dienes, such as tetrahydroindene; nonboradiene; methyl-tetrahydro 1 ndene; dicyclopentadiene (DCPD); bicyclo-(2.2.1)-hepta-2,5-diene; alkenyl, alkylidene, cycloalkenyl and cycloalkylidene norbornenes, such as 5-methylene-2-norbornene e (NM), 5-propenyl-2-norbornene, 5-isopropylidene-2-norbornene, 5-(4-cyclopentenyl)-2-norbornene, 5-cyclohexylidene-2-norbornene, and 5-vinyl-2-norbornene (VNB); e) cycloalkenyl-substituted alkenes, such as allyl cyclohexene, vinyl cyclooctene, allyl cyclodecene, vinyl cyclododecene. Of the non-conjugated dienes typically used, the preferred dienes are dicyclopentadiene, 1,4-hexadiene, 5-methylene-2-norbornene, and 5-ethylidene-2-norbornene, and tetracyclo (A-11,12) 5,8 dodecene. Particularly preferred diolefins are 5-ethylidene-2-norbornene (ENB), 1,4-hexadiene, dicyclopentadiene (DCPD), and 5-vinyl-2-norbornene (VNB).

Any of the polymers or oligomers produced by this invention, may be functionalized. Preferred functional groups include maleic acid and maleic anhydride. By functionalized is meant that the polymer has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha.methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight %, based upon the weight of the hydrocarbon resin and the unsaturated acid or anhydride.

EXAMPLES

The inventive and comparative metallocenes C1-C5, Comp1-Comp3 and Activators A1-A3 are shown below (where Me is methyl, Ph is phenyl, ). Preparations for C1-C5 are given. Metallocenes Comp1-Comp3 and Activators A1, A3 were obtained from commercial sources. Activator A2 was prepared according to WO 2003049856.

C1
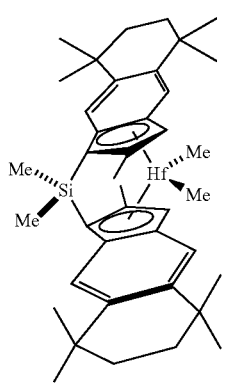

C2
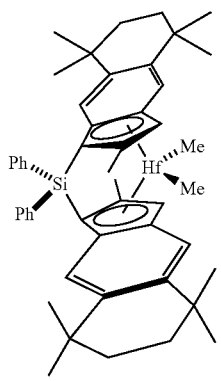

C3
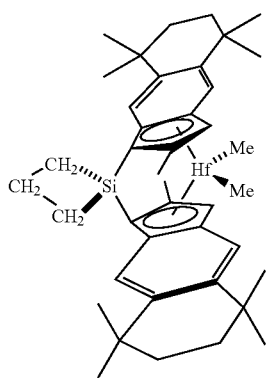

-continued

C4
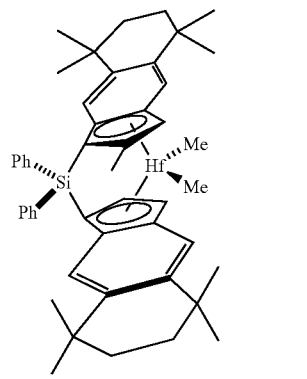

C5
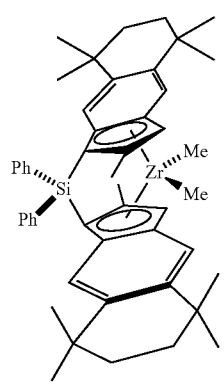

Comp1
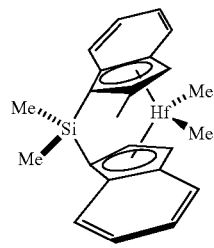

Comp2
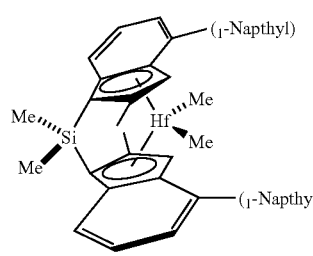

Comp3
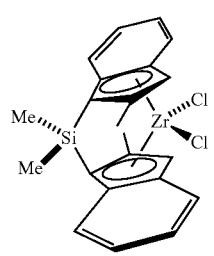

-continued

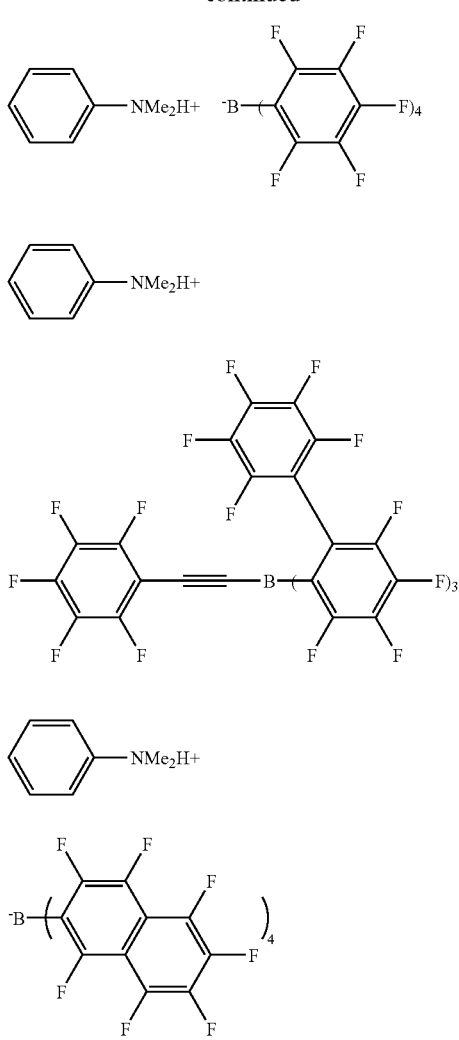

Propylene polymers were prepared in examples A, B, and L. Molecular weights (weight average molecular weight (Mw) and number average molecular weights (Mn) and polydispersity indices (Mw/Mn) were determined, versus polystyrene, using high throughput gel permeation chromatography measurement techniques disclosed in U.S. Pat. No. 6,475,391. Where indicated, thermal analyses were done using a TA Instruments DSC (Model 2920) by first heating the sample from −50 to 220° C. at 10° C./min, isotherm at 220° C. for 10 minutes, then cooling at 10° C./min from 150° C. to −100° C. and finally again heating to 150° C. at 10° C./min. The second heat results are reported.

Molecular weights for ethylene propylene copolymers prepared in examples C-K were measured by gel permeation chromatography using (1) an Alliance 2000 GPC3D equipped with differential refractive index (DRI) and viscometry detectors and an 18 angle light scattering detector calibrated using polystyrene standards or (2) a Polymer Labs 220 GPC 3D equipped with DRI, viscometry and an 3 angle light scattering detector. Samples were run in 1,2,4-trichlorobenzene (135° C.) using three Polymer Laboratories PC Gel mixed B LS columns in series.

Thermal analyses of the ethylene propylene copolymers prepared in examples C-K were conducted on a Pyris 1 instrument using the accompanying software available form Perkin Elmer Instruments, USA. Heat of fusion ($\Delta H_{fus}$ in the tables herein) were measured by Differential Scanning Calorimetry (DSC) using the ASTM E-794-95 procedure. All measurements were conducted during the first heating cycle between −100° C. and +150° C. on a sample that had been molded at 200° C. and allowed to anneal at room temperature for approximately 7 days. The first heating cycle was run at a temperature ramp rate of 20° C./min. The heat of fusion was measured from the total area under the peak curve in the region of room temperature to 105° C. The melting temperatures reported here are the peak melting temperatures from the second melt unless otherwise indicated. For polymers displaying multi-peak melting characteristics, the higher melting peak was taken as the principal melting point.

Composition measurements of the ethylene propylene copolymers prepared in examples C-J were conducted on a Perkin Elmer PE 1760 FTIR spectrophotometer. A thin homogeneous film of the copolymer was pressed at a temperature of about 150° C., or greater, then mounted on the spectrophotometer. A full spectrum of the sample from 600 to 4000 cm$^{-1}$ was recorded and the monomer weight percent of ethylene calculated from the equation: Ethylene wt %= 82.585−111.987X+30.045 X$^2$, wherein X is the ratio of the peak height at 1155 cm$^{-1}$ and peak height at either 722 or 732 cm$^{-1}$, whichever is higher.

For example K, $^{13}$C NMR measurements with and without proton decoupling were used to determine the composition, propylene triad tacticities ([mm]), regio error content, the reactivity ratio product (r1r2) and m/r ratios. Methods to determine these values are found in: Randall, J. Macromolecules 1978, 11, 33; Cozewith, C. Macromolecules 1987, 20, 1237; Tsutsui, T. et. al. Polymer, 1989, 30, 1350; U.S. Pat. No. 5,504,172 and references therein.

For example K, polymer samples for $^{13}$C NMR spectroscopy were dissolved in d$_2$-1,1,2,2-tetrachloroethane and the samples were recorded at 125° C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, Carbon-13 NMR Method", Academic Press, New York, 1977. The percent of methylene sequences of two in length, % (CH$_2$)$_2$, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Catalyst Synthesis Examples 5,6,7,8-tetrahydro-2,5,5,8,8-pentamethyl-benz[f]indene was prepared according to a published report (WO 99/46270) and converted to 5,6,7,8-tetrahydro-2,5,5,8,8-pentamethyl-benz[f]indenyl lithium by treatment with butyl lithium in pentane.

Example 1

Preparation of rac-Me$_2$Si(5,6,7,8-tetrahydro-2,5,5,8,8-pentamethyl-benz[f]indenyl)$_2$HfMe$_2$ (C1)

Example 1a

Preparation of Me$_2$Si(5,6,7,8-tetrahydro-2,5,5,8,8-pentamethyl-benz[f]indene)

5,6,7,8-tetrahydro-2,5,5,8,8-pentamethyl-benz[f]indenyl lithium (6 g, 24.4 mmol) was added, mostly as a solid, to a cold (−30° C.) solution of Me$_2$SiCl$_2$ (1.57 g, 12.2 mmol) and ether (150 mL). The color turned yellow. After stirring overnight the reaction was incomplete. THF (ca. 1 mL) was added and the reaction allowed to stir for a total of 6 days. The solution was then filtered through a glass frit then a 0.45 μm acrodisc. The solvent was removed by a nitrogen purge then the product was dried in vacuo. The yield was 6.31 g.

Example 1b

Preparation of rac-Me$_2$Si(5,6,7,8-tetrahydro-2,5,5,8,8-pentamethyl-benz[f]indenyl)$_2$HfCl$_2$ A solution of Me$_2$Si(5,6,7,8-tetrahydro-2,5,5,8,8-pentamethyl-benz[f]indene) (6.31 g, 11.75 mmol) and ether (325 mL) was treated with a solution of 1.6 M butyl lithium in hexane (14.7 mL, 23.52 mmol). The color turned orange. After stirring overnight, the slurry was cooled to −30 C (freezer) then stirred rapidly while HfCl$_4$ (3.75 g, 11.7 mmol) was added as a solid. The color turned intense yellow. After stirring ca. 1 day, the mixture was filtered giving the product with LiCl. Repeated extractions with CH$_2$Cl$_2$ (total 750 mL) gave the product in racemic form. Yield 2.72 g.

Example 1c

Preparation of rac-Me$_2$Si(5,6,7,8-tetrahydro-2,5,5,8,8-pentamethyl-benz[f]indenyl)$_2$HfMe$_2$ (C1)

A 3.0 M solution of MeMgBr in ether (0.33 mL, 1 mmol) and ca. 1 mL of ether was added to a solution of rac-Me$_2$Si(5,6,7,8-tetrahydro-2,5,5,8,8-pentamethyl-benz[f]indenyl)$_2$HfCl$_2$ (0.288 g, 0.39 mmol) and benzene (50 mL). The reaction was stirred overnight then additional grignard reagent (0.5 mL, 1.5 mmol) was added. The mixture was stirred over the weekend then heated to reflux overnight. The mixture was then treated with Me$_3$SiCl (0.2 mL, 1.57 mmol), 1,2-dimethoxyethane (0.25 mL, 2.4 mmol), filtered then dried. Yield 0.189 g.

Example 2

Preparation of rac-Ph$_2$Si(5,6,7,8-tetrahydro-2,5,5,8,8-pentamethyl-benz[f]indenyl)$_2$HfMe$_2$.(C2)

Example 2a

Preparation of Ph$_2$Si(5,6,7,8-tetrahydro-2,5,5,8,8-pentamethyl-benz[f]indene)$_2$ 5,6,7,8-tetrahydro-2,5,5,8,8-pentamethyl-benz[f]indenyl lithium (45.1 g, 183 mmol) was added to a solution of Ph$_2$Si(OSO$_2$CF$_3$)$_2$ (44.0 g, 91.6 mmol) and ether (500 mL). A small amount of ether was used to rinse the flask containing the lithium reagent. After stirring for three days, the reaction was washed with water (2×50 mL). The ether layer was dried with MgSO$_4$, filtered then the solvent was removed to give the product as a white solid. Yield 59.6 g (of which 0.6 wt % is ether).

Example 2b

Preparation of Ph$_2$Si(5,6,7,8-tetrahydro-2,5,5,8,8-pentamethyl-benz[f]indenyl lithium)$_2$.OEt$_2$ A 1.6 M solution of butyl lithium in hexane (112 mL, 179.2 mmol) was added to a solution of Ph$_2$Si(5,6,7,8-tetrahydro-2,5,5,8,8-pentamethyl-benz[f]indene)$_2$ (59.27 g, 89.7 mmol), dissolved in ether (1 L). The color changed from yellow to red. After the reaction was stirred over night, the solvent was removed with a purge of N$_2$. The remaining solids were slurried with pentane (200 mL) collected on a frit then rinsed with pentane until the solid was a yellow powder, then dried. Yield 63.85 g.

Example 2c

Preparation of rac-Ph$_2$Si(5,6,7,8-tetrahydro-2,5,5,8,8-pentamethyl-benz[f]indenyl)$_2$HfCl$_2$ as a mixture with LiCl A solution prepared from Ph$_2$Si(5,6,7,8-tetrahydro-2,5,5,8,8-pentamethyl-benz[f]indenyl lithium)$_2$.OEt$_2$ (10 g, 13.4 mmol) and ether (500 mL) was cooled to −30° C. then treated with HfCl$_4$ (4.17 g, 13.0 mmol). After stirring for two days, the yellow slurry was filtered and the solids rinsed with ether (3×30 mL) then dried. Yield 5.22 g.

Example 2d

Preparation of rac-Ph$_2$Si(5,6,7,8-tetrahydro-2,5,5,8,8-pentamethyl-benz[f]indenyl)$_2$HfMe$_2$ (C2)

A 3.0 M solution of MeMgBr in ether (2.6 mL, 7.8 mmol) was added to a slurry prepared from a mixture of rac-Ph$_2$Si(5,6,7,8-tetrahydro-2,5,5,8,8-pentamethyl-benz[f]indenyl)$_2$HfCl$_2$ (78 wt %) and LiCl (22 wt %) (2.58 g mixture, 2.01 g rac-Ph$_2$Si(5,6,7,8-tetrahydro-2,5,5,8,8-pentamethyl-benz[f]indenyl)$_2$HfCl$_2$, 1.91 mmol) and benzene (200 mL). The reaction was stirred for 2 hours then filtered (0.45 μm) and treated with Me$_3$SiCl (0.60 mL, 4.7 mmol). After stirring overnight, the gray mixture was treated with 1,4-dioxane (1.7 g, 19.3 mmol). After stirring for 1 hour, the cloudy mixture was filtered (4-8 μm) to yield a clear yellow filtrate. The benzene was removed and the solid mixed with toluene (20 mL) then the mixture was dried to remove excess 1,4-dioxane. The solid was rinsed with a small amount of pentane (5 mL) and dried in vacuo to give the product as a light yellow powder. Yield 1.31 g.

Example 3

Preparation of rac-(CH2)$_3$Si(5,6,7,8-tetrahydro-2,5,5,8,8-pentamethyl-benz[f]indenyl)$_2$HfMe$_2$.(C3)

Example 3a

Preparation of (CH$_2$);Si(5,6,7,8-tetrahydro-2,5,5,8,8-pentamethyl-benz[f]indene)$_2$ 5,6,7,8-tetrahydro-2,5,5,8,8-pentamethyl-benz[f]indenyl lithium (5 g, 20.5 mmol) was added to a solution of (CH$_2$)$_3$ SiCl$_2$ (1.45 g, 10.3 mmol) and ether (200 mL). After stirring overnight the solvent was removed and the solids extracted with pentane (3×50 mL), filtered then dried in vacuo to give a white solid. Yield 5.06 g.

Example 3b

Preparation of (CH$_2$)$_3$Si(5,6,7,8-tetrahydro-2,5,5,8,8-pentamethyl-benz[f]indenyl lithium)$_2$.Et$_2$O 1.6 M Butyl lithium in hexane (11.6 mL, 18.56 mmol) was added to a solution (CH$_2$)$_3$Si(5,6,7,8-tetrahydro-2,5,5,8,8-pentamethyl-benz[f]indene)$_2$ (5.06 g, 9.29 mmol) in ether (100 mL). The initially clear yellow solution became an orange slurry. After stirring overnight, the mixture was filtered and the light yellow solid was washed with pentane (2×20 mL) then dried. Yield 4.28 g.

Example 3c

Preparation of rac-(CH$_2$)$_3$Si(5,6,7,8-tetrahydro-2,5,5,8,8-pentamethyl-benz[f]indenyl)$_2$HfCl$_2$ HfCl$_4$ (2.17 g, 6.77 mmol) was added to a slurry prepared from (CH$_2$)$_3$Si(5,6,7,8-tetrahydro-2,5,5,8,8-pentamethyl-benz[f]indenyl lithium)$_2$.Et$_2$O (4.28 g, 6.77 mmol) and ether (100 mL). The color turned intense yellow. After stirring overnight, the mixture was filtered and the solid washed with ether (2×10 mL) then pentane (3×10 mL). The solid was dried overnight. Yield 2.74 g.

Example 3d

Preparation of rac-(CH$_2$)$_3$Si(5,6,7,8-tetrahydro-2,5,5,8,8-pentamethyl-benz[f]indenyl)$_2$HfMe$_2$.(C3)

3 M Methylmagnesium bromide in ether (2.75 mL, 8.25 mmol) was added to a mixture of rac-(CH$_2$)$_3$Si(5,6,7,8-tetrahydro-2,5,5,8,8-pentamethyl- benz[f]indenyl)$_2$HfCl$_2$ (2.05 g, 2.03 mmol) and toluene (100 mL). After stirring overnight, the mixture was treated with Me$_3$SiCl (0.54 mL, 4.25 mmol), stirred overnight, then treated with 1,4-dioxane (1.91 g, 21.7 mmol). After stirring for 4 hours, the mixture was filtered and the remaining solids further washed with toluene (5 mL). The filtrate was dried then washed with pentane (10 mL) then dried. Yield 1.1 g.

Example 4

Preparation of rac-Ph$_2$Si(5,6,7,8-tetrahydro-5,5,8,8-tetramethyl-benz[f]indenyl$_2$HfMe$_2$.(C4)

Example 4a

Preparation of 5,6,7,8-tetrahydro-5,5,8,8-tetramethyl-benz[f]indan-2-one

A 1 L 3-neck flask was charged with AlCl$_3$ (80.8 g, 0.606 mol), fitted with a mechanical stirrer, and a 250 mL addition funnel, charged with anhydrous methylene chloride (370 mL). The slurry was cooled to −20° C. and stirred. The addition funnel was then charged with (in two portions over the course of the reaction) with a solution of 2-indanone (40.0 g, 0.303 mol) {Note: Aldrich brand 2-indanone was rinsed with ether to remove brown impurities}, 2,5-dichloro, 2,5-dimethylhexane (55.4 g, 0.303 mol) and anhydrous methylene chloride (180 mL). The solution was dripped onto the cold, stirring AlCl$_3$ slurry over the course of 50 min. After stirring for 2.5 h after the addition was complete, a solution of 2,5-dichloro, 2,5-dimethylhexane (13 g, 0.071 mol) and anhydrous methylene chloride (42 mL). After stirring an additional hour, the reaction mixture was poured onto ice (1 L) and treated with ether (500 mL). The organic layer was separated and the aqueous layer extracted with ether (2×200 mL). The combined organic layers were washed with 2.5 M NaCl (aq) (3×75 mL) then water (25 mL) then dried over MgSO$_4$. The dried organic solution was filtered into a 3 L flask and the solvent was slowly removed with a nitrogen blowing over the surface of the solution. The solid that remained was washed with cold pentane and the solids isolated by filtration. The product, a fine crystalline material, was separated manually from a small amount of chunky oily solids that contained product and an impurity. Yield 21 g.

Example 4b

Preparation of 5,6,7,8-tetrahydro-5,5,8,8-tetramethyl-benz[f]indan-2-tosylhydrazone A 500 mL flask was charged with tosylhydrazide (7.68 g, 41.3 mmol), 5,6,7,8-tetrahydro-5,5,8,8-tetramethyl-benz[f] indan-2-one (10.0 g, 1 equiv.) and anhydrous ether then stirred mechanically under nitrogen overnight. The slurry was filtered, rinsed with cold ether then dried. Yield 13.85 g

Example 4c

Preparations of 5,6,7,8-tetrahydro-5,5,8,8-tetramethyl-benz[f]indene and 5,6,7,8-tetrahydro-5,5,8,8-tetramethyl-benz[f]indenyl lithium.0.83 DME A 1 L flask was charged with of 5,6,7,8-tetrahydro-5,5,8,8-tetramethyl-benz[f]indan-2-tosylhydrazone (13.85 g, 33.7 mmol), anhydrous 1,2-dimethoxyethane (500 mL) (1,2-dimethoxyethane=DME) then 1.77 M BuLi (in hexane) (38 mL, 2 equiv.). The color turned dark. The mixture was heated at reflux for 60 min then allowed to cool to room temperature overnight. Part of the resulting slurry (white precipitate) in burgundy colored solution was filtered and the 1,2-dimethoxyethane removed from the filtrate leaving the product, 5,6,7,8-tetrahydro-5,5,8,8-tetramethyl-benz[f]indenyl lithium.0.83 DME as a white solid with a trace of purple color, after washing repeatedly with pentane. Yield 1.76 g The remainder of the solution was quenched with water (20 mL) then washed with 4 M NaCl (3×100 mL). The organic layer was then dried over MgSO$_4$ then reduced to a brown solid. Yield 5.5 g. This product was further purified by sublimation at 75° C. using a vacuum pump. Yield 4.1 g of 5,6,7,8-tetrahydro-5,5,8,8-tetramethyl-benz[f]indene as a white solid.

Example 4d

Preparation of 5,6,7,8-tetrahydro-5,5,8,8-tetramethyl-benz[f]indene

A 1 L flask was charged with of 5,6,7,8-tetrahydro-5,5,8,8-tetramethyl-benz[f]indan-2-tosylhydrazone (12.81 g, 31.2 mmol), anhydrous 1,2-dimethoxyethane (500 mL) then 1.64 M BuLi (in hexane) (38 mL, 2 equiv.). The color turned dark. The mixture was heated at reflux for 75 min then allowed to cool to room temperature overnight. The mixture was treated with water (20 mL) then washed with 4 M NaCl (3×100 mL). The organic layer was then dried over $MgSO_4$ then reduced to a brown solid. Yield 7.23 g. This product was further purified by sublimation.

Example 4e

Preparation of $Ph_2Si(5,6,7,8$-tetrahydro-5,5,8,8-tetramethyl-benz[f]indene$)_2$ A stirred slurry of, 5,6,7,8-tetrahydro-5,5,8,8-tetramethyl-benz[f]indenyl lithium.0.83 DME (1.76 g, 5.73 mmol) and ether (50 mL) was treated with $Ph_2Si(OSO_2CF_3)_2$ (1.39 g, ½ equiv.) and ether (60 mL). After stirrung for 2 hours, the mixture was washed with 2 M NaCl (3×10 mL), dried over $MgSO_4$ then reduced to a solid. Yield 1.76 g.

Example 4f

Preparation of rac-$Ph_2Si(5,6,7,8$-tetrahydro-5,5,8,8-tetramethyl-benz[f]indenyl$)_2HfCl_2$ $Ph_2Si(5,6,7,8$-tetrahydro-5,5,8,8-tetramethyl-benz[f]indene$)_2$ (1.76 g, 2.78 mmol) and ether (40 mL) were treated with 1.77 M BuLi (in hexane) (3.2 mL, 5.66 mmol) and stirred overnight. Additional 1.77 M BuLi (in hexane) (0.35 mL, 0.62 mmol) was added. This mixture was treated with 1.0 M $Me_3SnCl$ (5.8 mL, 5.8 mmol) then filtered to remove the LiCl. The ether was removed in vacuo and the glassy solid dissolved in toluene and filtered (0.45 µm) onto a slurry of $HfCl_4$ (0.89 g, 2.78 mmol) and toluene (20 mL). The color turned red. $^1H$ NMR showed broad resonances and a clear set for the rac-metallocene. Filtered, removed toluene and unsuccessfully attempted crystallization from ether. Removed ether then washed with pentanes (5×10 mL) to remove impurities. Then took up material in benzene (25 mL), filtered and dried in-vacuo. Yield 554 mg.

Example 4g

Preparation of rac-$Ph_2Si(5,6,7,8$-tetrahydro-5,5,8,8-tetramethyl-benz[f]indenyl$)_2HfMe_2$ (C4)

A 3.0 M solution of MeMgBr in ether (1.15 mL, 3.45 mmol) was added to a solution of rac-$Ph_2Si(5,6,7,8$-tetrahydro-5,5,8,8-tetramethyl-benz[f]indenyl$)_2HfCl_2$ (0.5 g, 0.568 mmol) and toluene (50 mL). The reaction was stirred overnight then heated to 75° C. for 2 h then cooled to room temperature then treated with $Me_3SiCl$ (0.30 mL, 2.36 mmol). After stirring overnight, the mixture was treated with 1,4-dioxane (0.77 g, 8.74 mmol). After stirring for 4 h, the mixture was filtered then the solids were washed with toluene (2 ×50 mL). The solvent was removed and the residue taken up in pentane and filtered (0.45 µm). The pentane was removed to yield rac-$Ph_2Si(5,6,7,8$-tetrahydro-5,5,8,8-tetramethyl-benz[f]indenyl$)_2HfMe_2$ as a glassy solid. Yield 0.27 g.

Example 5

Preparation of rac-$Ph_2Si(5,6,7,8$-tetrahydro-2,5,5,8,8-pentamethyl-benz[f]indenyl$)_2ZrCl_2$.(C5) MAO/Silica Catalyst

Example 5a

Preparation of rac-$Ph_2Si(5,6,7,8$-tetrahydro-2,5,5,8,8-pentamethyl-benz[f]indenyl$)_2ZrCl_2$.(C5)

To a slurry of cold (−30° C.) $Ph_2Si(5,6,7,8$-tetrahydro-2,5,5,8,8-pentamethyl-benz[f]indenyl lithium$)_2$ (2 g, 3 mmol) and ether (100 mL) was added $ZrCl_4$ (0.7 g, 3 mmol). The mixture became homogeneous then a precipitate was observed. After stirring overnight, the solvent was removed and the mixture washed with pentane (12×20 mL). The rac isomer remained with the salts on the frit. Yield 0.88 g (ca. 71 wt % metallocene). A sample of this mixture (0.2 g) was extracted with $CH_2Cl_2$ to obtain metallocene free of salts.

Example 5b

Preparation of rac-$Ph_2Si(5,6,7,8$-tetrahydro-2,5,5,8,8-pentamethyl-benz[f]indenyl$)_2ZrCl_2$ and MAO supported on silica A mixture of 30 wt % MAO in toluene (983 mg, 16.2 mmol) and toluene (10 mL) was added to a mixture of rac-$Ph_2Si(5,6,7,8$-tetrahydro-2,5,5,8,8-pentamethyl-benz[f]indenyl$)_2ZrCl_2$ (15.7 mg, 0.0191 mmol) and toluene (5 mL). The green solution was added to silica (1.01 g). The color turned red. After stirring for 15 min the mixture was filtered. The supported catalyst was dried in vacuo overnight.

Polymerization Examples

Examples A1-A66

Semibatch Propylene Polymerizations

Polymerizations were conducted in autoclaves lined with glass test tubes (internal volume of reactor=23.5 mL). The autoclaves were charged with a 1 mM hexane solution of $AlOCt_3$ (0.1 mL, 1 µmol), hexane (see Table 1 for amount), a 200 µM toluene solution of $PhNMe_2H^+B(C_6F_5)_4^-$ (0.1 mL, 0.02 µmol) and pressurized with propylene at the temperature indicated in the tables. Then a 200 µM solution of catalyst (0.1 mL, 0.02 µmol) was added to the autoclave. Propylene was allowed to flow into the autoclaves during polymerization. Polymerizations were halted by addition of an $O_2$/Ar gas mixture to the cells. The reactors were then vented and cooled. Polymer was isolated after the solvent was removed in-vacuo. Polymerization data are reported in Tables 1-3.

Examples B1-B67

Batch Propylene Polymerizations

Polymerizations were performed in glass-lined 22.5 mL reactor equipped with a mechanical stirrer, an external heater for temperature control, septum inlet and regulated supply of nitrogen, ethylene, and propylene in an inert atmosphere of a nitrogen glove box. The reactor was dried and degassed at 115° C. for 5 hours and then purged with nitrogen at room temperature for another five hours. It was finally purged with propylene gas at 50 psig. Hexane, scavenger (2 µmol of trin-octylaluminum) and propylene were added at room temperature. The reactor was heated to process temperature while stirring at 800 rpm. The activator and catalyst, 20 μmol of each in 0.1 mL of toluene, were injected at process conditions. The reaction was run to a predetermined time period (43 seconds unless otherwise noted) at the end of which it was quenched with 5 mol % Oxygen in Argon. The reactor was then cooled, vented and the polymer recovered by vacuum centrifugation of the reaction mixture. Polymerization data are reported in Tables 4-6.

The amounts of hexane and propylene in the reactors for the given reaction temperature are reported in Table 4.

Examples C-J

General Procedure for Continuous Ethylene/Propylene Copolymerizations

Polymerizations were conducted in a 980 mL continuous feed stirrred tank polymerization reactor. The reactor pressure was maintained at 320 psi by a restriction on the outflow of the polymerization reactor and agitated with a twin three bladed pitched propeller type agitator at about 550 rpm. Reactor feeds (hexane, ethylene, propylene and a solution of tri-(n-octyl)aluminum (TNOA) in hydrocarbon were continuously fed into the reactor at flow rates indicated in Tables 7-14. These feeds were refrigerated prior to introduction into the reactor to maintain the polymerization temperature. A catalyst solution, prepared by mixing catalyst and activator in toluene was fed separately into the reactor at flow rates indicated in Tables 7a-14a. The polymerization was rapid and representative samples were collected after 4 residence times at steady state. Polymer samples were dried and their mass used to calculate the polymerization rates, which are reported with other polymer characterization data in Tables 7b-14b.

Examples C1-C9

Copolymerization using C1/A1

The catalyst solution was prepared from C1 (0.105 g, 1.41× $10^{-4}$ mol), A1 (0.115 g, 1.43×$10^{-4}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 7a and 7b.

Examples D1-D3

Copolymerization using C2/A1

The catalyst solution was prepared from C2 (0.122 g, 1.41× $10^{-4}$ mol), A1 (0.115 g, 1.43×$10^{-4}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 8a and 8b.

Examples E1-E8

Copolymerization using C2/A1

The catalyst solution was prepared from C2 (0.062 g, 7.1× $10^{-5}$ mol), A1 (0.057 g, 7.1×$10^{-5}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 9a and 9b.

Examples F1-F4

Copolymerization using C1/A3

The catalyst solution was prepared from C1 (0.052 g, 7.0× $10^{-5}$ mol), A3 (0.079 g, 6.9×$10^{-5}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 10a and 10b.

Examples G1-G3

Copolymerization using C1/A3

The catalyst solution was prepared from C1 (0.026 g, 3.5× $10^{-5}$ mol), A3 (0.04 g, 3.5×$10^{-5}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 11a and 11b.

Examples H1-H8

Copolymerization using C2/A3

The catalyst solution was prepared from C2 (0.062 g, 7.1× $10^{-5}$ mol), A3 (0.082 g, 7.2×$10^{-5}$ mol) and anhydrous, deoxygenated toluene (900 mL). The TNOA solution was 0.198 wt % solution of tri-(n-octyl)aluminum (TNOA) in hydrocarbon (3.155 g heptane, 527.2 g hexane)). Polymerization conditions and results are, respectively, reported in Tables 12a and 12b.

Examples I1-I2

Copolymerizations using C4/A1

The catalyst solution was prepared from C4 (0.0574 g, 7.60×$10^{-5}$ mol), A1 (0.06 g, 7.49×$10^{-5}$ mol) and anhydrous, deoxygenated toluene (900 mL). The aluminum alkyl solution was prepared from $AlOct_3$ (1.0515 g) and anhydrous, deoxygenated toluene (800 mL). Polymerization conditions and results are, respectively, reported in Tables 13a and 13b.

Example I3

Copolymerizations using C4/A1

The catalyst solution was prepared from C4 (0.1 g, 1.32× $10^{-4}$ mol), A1 (0.098 g, 1.22×$10^{-4}$ mol) and anhydrous, deoxygenated toluene (900 mL). ). The aluminum alkyl solution was prepared from $AlOct_3$ (1.0515 g) and anhydrous, deoxygenated toluene (800 mL). Polymerization conditions and results are, respectively, reported in Tables 13a and 13b.

Example J1

Copolymerization using C3/A1

The catalyst solution was prepared from C3 (0.1 g, 1.15× $10^{-4}$ mol), A1 (0.097 g, 1.21×$10^{-4}$ mol) and anhydrous, deoxygenated toluene (900 mL). ). The aluminum alkyl solution was prepared from AlOct$_3$ (1.0515 g) and anhydrous, deoxygenated toluene (800 mL). Polymerization conditions and results are, respectively, reported in Tables 14a and 14b.

Examples J2-J4

Copolymerizations using C3/A1

The catalyst solution was prepared from C3 (0.138 g, 1.59×10$^{-4}$ mol), A1 (0.097 g, 1.68×10$^{-4}$ mol) and anhydrous, deoxygenated toluene (900 mL). The aluminum alkyl solution was prepared from AlOct$_3$ (1.0515 g) and anhydrous, deoxygenated toluene (800 mL). Polymerization conditions and results are, respectively, reported in Tables 14a and 14b.

Examples K1-K11

Continuous Ethylene Propylene Copolymerizations using C2/A1

Polymerizations were conducted in a 27 L continuous feed stirred tank polymerization reactor agitated with a twin three bladed pitched propeller type agitator at 700 rpm. The reactor pressure was maintained at 1600 psig so that all regions in the polymerization zone were liquid full and had the same composition during the entire course of the polymerization. Hexane, ethylene, propylene, 0.3 wt % tri-(n-octyl)aluminum (TNOA) in hexane were continuously fed into the reactor. Separately, a catalyst solution, prepared by mixing C2 (1.35 g, 1.56 mmol) and A1 (1.5 g, 1.87 mmol) in oxygen-free anhydrous toluene (4 L) was fed into the reactor. Feed conditions for the copolymerization are reported in Table 15a. Polymerizations were conducted at temperatures between 60 and 140° C. The heat of polymerization was removed by adding pre-chilled hexane. Small polymer samples were taken directly from the reactor during steady state operation and analyzed. Polymer production, catalyst efficiency and polymer properties of the sampled polymers are reported in Table 15b. After quenching the polymerization with a solution of water in hexane, the polymer produced were recovered by a two stage solvent removal process. First, 70% of the solvent was removed in a lower critical solution temperature process then the remaining solvent was removed in a LIST devolatization extruder. The solvent removed in the first stage was dried by passing through a column filled with 3 Å and Selexsorb CD molecular sieves and recycled back to reactor. The solvent removed in the second stage was slopped. The polymer was finished in pellets about a ⅛ to ¼ inch in principal axes.

Examples L1-L16

Propylene Polymerization with Supported Catalyst

Polymerizations were performed in dry glass-lined 22.5 mL reactor equipped with a mechanical stirrer, an external heater for temperature control, septum inlet and regulated supply of nitrogen, hydrogen/nitrogen gas mixture (20/80), and propylene in an inert atmosphere of nitrogen glove box. The reactor was dried then charged with a hydrogen nitrogen gas mixture (20 H$_2$:80 N$_2$) then propylene, 0.1 M AlOct$_3$ and hexane. The reactor was heated to 70° C. then a gradient of 0.69 wt % slurries of catalyst supported on silica/MAO in toluene were injected into the reactor. The feed conditions for these experiments are reported in Table 16a. The polymerizations were halted after 30 min. then quenched with 5 mol % oxygen in argon. The reactor was then cooled, vented and the polymer recovered by vacuum centrifugation of the reaction mixture. The polymer was characterized by GPC (vs polystyrene standards). Polymerization data are reported in Table 16b.

Stress Strain Behavior of EP Copolymers Prepared in Continuous Solution Copolymerizations Polymer ($\geqq$72 g) prepared in the continues solution was homogenized in a Brabender intensive mixture for 3 minutes at a temperature controlled to be within 180-220° C. High shear roller blades were used for the mixing and approximately 0.4 g of Irganox-1076, an antioxidant available from the Novartis Corporation, was added to the blend. At the end of the mixing, the mixture was removed and pressed out into a 6"×6" mold into a pad 025" thick at 215° C. for 3 to 5 min. At the end of this period, the pad was cooled for 2.5 min and removed and allowed to anneal for 40-48 h. Test specimens of the required dumbbell geometry were removed from this pad and evaluated on an Instron tester to produce the data shown in Table 17. Young's Modulus, Ultimate elongation and Ultimate tensile were determined according to ASTM D638 and modulus data at 50%, 100%, 200% and 500% was recorded for the test done according to ASTM D638.

Composition Distribution Determination of EP Copolymers Prepared in Continuous Solution Copolvmerizations Composition distribution of the polymers as described above was measured as described below. About 30 g of the second polymer component was cut into small cubes about ⅛" on the side. This is introduced into a thick walled glass bottle closed with screw cap along with 50 mg of Irganox1076, an antioxidant commercially available from Ciba-Geigy Corporation. Then, 425 mL of hexane (a principal mixture of normal and ISO isomers) is added to the contents of the bottle and the sealed bottle is maintained at about 23° C. for 24 h. At the end of this period, the solution is decanted and the residue is treated with additional hexane for an additional 24 h. At the end of this period, the two-hexane solutions are combined and evaporated to yield a residue of the polymer soluble at 23° C. To the residue is added sufficient hexane to bring the volume to 425 mL and the bottle is maintained at about 31° C. for 24 h in a covered circulating water bath. The soluble polymer is decanted and the additional amount of hexane is added for another 24 hours at about 31° C. prior to decanting. In this manner, fractions of the second polymer component soluble at 40, 48, 55, and 62° C. are obtained at temperature increases of approximately 8° C. between stages. Further, increases in temperature to 95° C. can be accommodated, if heptane, instead of hexane, is used as the solvent for all temperatures above about 60° C. The soluble polymers are dried, weighed and analyzed for composition, as wt % ethylene content, by the IR technique described above. Soluble fractions obtained in the adjacent temperature increases are the adjacent fractions in the specification above. Results are reported in Table 18.

TABLE 1

Example A. Monomer Feed Conditions[a]

| | | |
|---|---|---|
| T (° C.) | 40 | 75 |
| Hexane (mL) | 2.127 | 1.997 |
| Toluene (mL) | 0.2 | 0.2 |
| Propylene Pressure (psig) | 37 | 85 |
| Catalyst (micromoles) | 0.02 | 0.02 |
| Al(Oct)$_3$ (micromoles) | 1 | 1 |

[a]Total amounts of reagents in autoclave at initiation of polymerization.

TABLE 2

Examples A1-A66. Semibatch Propylene Polymerization Data

| Example | Metallocene/Activator | Mw | Mw/Mn | Temp (° C.) | Yield | Polymer Tm |
|---|---|---|---|---|---|---|
| A-1 | Comp2/A1 | 1360181 | 1.69 | 40 | 0.0182 | |
| A-2 | Comp2/A1 | 1232499 | 1.66 | 40 | 0.0165 | |
| A-3 | Comp2/A1 | 1137802 | 1.66 | 40 | 0.0211 | |
| A-4 | Comp2/A1 | 935247 | 1.77 | 40 | 0.0738 | |
| A-5 | Comp2/A1 | 689884 | 1.79 | 40 | 0.0988 | |
| A-6 | Comp2/A1 | 1255412 | 1.52 | 40 | 0.0315 | |
| A-7 | Comp2/A1 | 1314435 | 1.65 | 40 | 0.0415 | 164.09, 154.34 |
| A-8 | Comp2/A1 | 1262111 | 1.75 | 40 | 0.0526 | |
| A-9 | Comp2/A1 | 1033984 | 1.72 | 40 | 0.0528 | |
| A-10 | Comp2/A1 | 1011980 | 1.74 | 40 | 0.0281 | |
| A-11 | Comp2/A1 | 1083342 | 1.76 | 40 | 0.0617 | |
| A-12 | Comp2/A1 | 999616 | 1.69 | 40 | 0.0309 | |
| A-13 | Comp2/A1 | 1073986 | 1.71 | 40 | 0.0411 | |
| A-14 | Comp2/A1 | 1185897 | 1.73 | 40 | 0.0264 | |
| A-15 | Comp2/A1 | 1188284 | 1.67 | 40 | 0.0315 | |
| A-16 | Comp2/A1 | 1100556 | 1.74 | 40 | 0.0271 | |
| A-17 | Comp2/A1 | 218840 | 1.62 | 75 | 0.0356 | |
| A-18 | Comp2/A1 | 187897 | 1.71 | 75 | 0.0796 | |
| A-19 | Comp2/A1 | 175380 | 1.64 | 75 | 0.0837 | |
| A-20 | Comp2/A1 | 152318 | 1.60 | 75 | 0.1359 | |
| A-21 | Comp2/A1 | 155605 | 1.56 | 75 | 0.1265 | |
| A-22 | Comp1/A1 | 525429 | 1.70 | 40 | 0.0933 | |
| A-23 | Comp1/A1 | 528591 | 1.67 | 40 | 0.0852 | |
| A-24 | Comp1/A1 | 514103 | 1.70 | 40 | 0.1242 | |
| A-25 | Comp1/A1 | 476069 | 1.81 | 40 | 0.151 | |
| A-26 | Comp1/A1 | 469304 | 1.83 | 40 | 0.171 | |
| A-27 | Comp1/A1 | 523090 | 1.65 | 40 | 0.1699 | |
| A-28 | Comp1/A1 | 669610 | 1.56 | 40 | 0.0789 | 139.42 |
| A-29 | Comp1/A1 | 624085 | 1.56 | 40 | 0.0918 | |
| A-30 | Comp1/A1 | 733533 | 1.76 | 40 | 0.0228 | |
| A-31 | Comp1/A1 | 587852 | 1.75 | 40 | 0.0719 | |
| A-32 | Comp1/A1 | 575723 | 1.67 | 40 | 0.1044 | |
| A-33 | Comp1/A1 | 551901 | 1.72 | 40 | 0.0741 | |
| A-34 | Comp1/A1 | 666727 | 1.69 | 40 | 0.0296 | |
| A-35 | Comp1/A1 | 411251 | 1.72 | 40 | 0.1051 | |
| A-36 | Comp1/A1 | 565723 | 1.65 | 40 | 0.0773 | |
| A-37 | Comp1/A1 | 582961 | 1.66 | 40 | 0.0837 | |
| A-38 | Comp1/A1 | 543852 | 1.70 | 40 | 0.0829 | |
| A-39 | Comp1/A1 | 131368 | 1.61 | 75 | 0.0868 | |
| A-40 | Comp1/A1 | 147248 | 1.70 | 75 | 0.0988 | |
| A-41 | Comp1/A1 | 113230 | 1.56 | 75 | 0.1143 | |
| A-42 | Comp1/A1 | 106186 | 1.54 | 75 | 0.1549 | 126.97 |
| A-43 | Comp1/A1 | 107889 | 1.57 | 75 | 0.1657 | |
| A-44 | C1/A1 | 967297 | 1.68 | 40 | 0.2163 | |
| A-45 | C1/A1 | 985383 | 1.66 | 40 | 0.2007 | |
| A-46 | C1/A1 | 902080 | 1.74 | 40 | 0.2664 | |
| A-47 | C1/A1 | 751598 | 1.82 | 40 | 0.218 | |
| A-48 | C1/A1 | 851656 | 1.93 | 40 | 0.256 | |
| A-49 | C1/A1 | 902545 | 1.97 | 40 | 0.2567 | |
| A-50 | C1/A1 | 1047008 | 1.66 | 40 | 0.2063 | 136.6 |
| A-51 | C1/A1 | 1204014 | 1.62 | 40 | 0.1705 | |
| A-52 | C1/A1 | 986381 | 1.70 | 40 | 0.2442 | |
| A-53 | C1/A1 | 1092381 | 1.78 | 40 | 0.182 | |
| A-54 | C1/A1 | 1190085 | 1.81 | 40 | 0.1653 | |
| A-55 | C1/A1 | 1040966 | 1.85 | 40 | 0.2469 | |
| A-56 | C1/A1 | 1320134 | 1.75 | 40 | 0.128 | |
| A-57 | C1/A1 | 1006150 | 1.88 | 40 | 0.2048 | |
| A-58 | C1/A1 | 1250139 | 1.80 | 40 | 0.1936 | |
| A-59 | C1/A1 | 1310244 | 1.79 | 40 | 0.1809 | |
| A-60 | C1/A1 | 1273133 | 1.68 | 40 | 0.1796 | |
| A-61 | C1/A1 | 269748 | 1.85 | 75 | 0.1824 | |
| A-62 | C1/A1 | 257174 | 1.88 | 75 | 0.2253 | |
| A-63 | C1/A1 | 250578 | 1.86 | 75 | 0.2084 | |
| A-64 | C1/A1 | 223473 | 1.98 | 75 | 0.2442 | |
| A-65 | C1/A1 | 291737 | 1.70 | 75 | 0.1807 | 132.39 |
| A-66 | C1/A1 | 264872 | 1.72 | 75 | 0.2418 | |

TABLE 3

Example A. Summary of Semibatch Propylene Polymerization Data

| Metallocene/Activator | Temp (° C.) | Avg Mw (g/mol) | Std. Dev. Mw (g/mol) | Number of Experiments |
|---|---|---|---|---|
| C1/A1 | 40 | 1063600 | 140580 | 17 |
| Comp1/A1 | 40 | 561753 | 60257 | 17 |
| Comp2/A1 | 40 | 1116576 | 125502 | 16 |
| C1/A1 | 75 | 259597 | 15855 | 6 |
| Comp1/A1 | 75 | 121184 | 14499 | 5 |
| Comp2/A1 | 75 | 178008 | 20288 | 5 |

TABLE 4

Example B. Monomer Feed Conditions for Batch Propylene Polymerizations

| Reaction Temperature | Hexane (mL) | Propylene (mL) |
|---|---|---|
| 40° C. | 3.965 | 0.628 |
| 70° C. | 3.805 | 0.704 |
| 100° C. | 3.690 | 0.795 |

TABLE 5

Examples B1-B87. Batch Propylene Polymerization Data

| Example | Metallocene/Activator | Temp (° C.) | Yield (g) | Mw (g/mol) | Mw/Mn | Tm (° C.) | Hf (J/g) |
|---|---|---|---|---|---|---|---|
| B-1 | Comp1/A1 | 40 | 0.0151 | 648330 | 1.5 | | |
| B-2 | Comp1/A1 | 40 | 0.0168 | 682091 | 1.4 | | |
| B-3 | Comp1/A1 | 40 | 0.0171 | 647855 | 1.5 | | |
| B-4 | Comp1/A1 | 40 | 0.0155 | 682145 | 1.5 | | |
| B-5 | Comp2/A1 | 40 | 0.0142 | 1237555 | 1.5 | | |
| B-6 | C2/A1 | 40 | 0.0128 | 2132896 | 1.3 | | |
| B-7 | C2/A1 | 40 | 0.0135 | 2166262 | 1.3 | | |
| B-8 | C2/A1 | 40 | 0.0101 | 2032035 | 1.3 | | |
| B-9 | C2/A1 | 40 | 0.0126 | 2549407 | 1.3 | | |
| B-10 | C1/A1 | 40 | 0.0126 | 2105520 | 1.4 | | |
| B-11 | Comp1/A1 | 70 | 0.0215 | 214255 | 1.4 | | |
| B-12 | Comp1/A1 | 70 | 0.0337 | 201936 | 1.5 | | |
| B-13 | Comp1/A1 | 70 | 0.0216 | 215022 | 1.4 | | |

TABLE 5-continued

Examples B1-B87. Batch Propylene Polymerization Data

| Example | Metallocene/Activator | Temp (° C.) | Yield (g) | Mw (g/mol) | Mw/Mn | Tm (° C.) | Hf (J/g) |
|---|---|---|---|---|---|---|---|
| B-14 | Comp1/A1 | 70 | 0.031 | 204352 | 1.5 | | |
| B-15 | Comp1/A1 | 70 | 0.0257 | 223219 | 1.4 | | |
| B-16 | Comp1/A1 | 70 | 0.0246 | 214879 | 1.4 | | |
| B-17 | Comp1/A1 | 70 | 0.0339 | 195381 | 1.4 | | |
| B-18 | Comp1/A1 | 70 | 0.0374 | 190041 | 1.4 | 135 | 76 |
| B-19 | Comp1/A1 | 70 | 0.0394 | 217926 | 1.4 | | |
| B-20 | Comp1/A1 | 70 | 0.0339 | 222444 | 1.4 | | |
| B-21 | Comp1/A1 | 70 | 0.034 | 205137 | 1.4 | | |
| B-22 | Comp1/A1 | 70 | 0.0359 | 198796 | 1.4 | | |
| B-23 | Comp1/A1 | 70 | 0.0174 | 206379 | 1.4 | | |
| B-24 | Comp1/A1 | 70 | 0.0399 | 211205 | 1.4 | | |
| B-25 | Comp2/A1 | 70 | 0.0248 | 265047 | 1.5 | | |
| B-26 | Comp2/A1 | 70 | 0.0283 | 256103 | 1.5 | | |
| B-27 | Comp2/A1 | 70 | 0.0263 | 278984 | 1.5 | | |
| B-28 | Comp2/A1 | 70 | 0.0236 | 253721 | 1.5 | | |
| B-29 | C2/A1 | 70 | 0.0287 | 1005952 | 1.5 | | |
| B-30 | C2/A1 | 70 | 0.0245 | 996420 | 1.5 | | |
| B-31 | C2/A1 | 70 | 0.0228 | 1022520 | 1.5 | | |
| B-32 | C2/A1 | 70 | 0.0216 | 941040 | 1.5 | | |
| B-33 | C1/A1 | 70 | 0.0298 | 741315 | 1.5 | | |
| B-34 | C1/A1 | 70 | 0.0359 | 687730 | 1.5 | 134 | 70 |
| B-35 | C1/A1 | 70 | 0.034 | 818005 | 1.5 | 136 | 75 |
| B-36 | C1/A1 | 70 | 0.0357 | 818694 | 1.5 | 133 | 76 |
| B-37 | C1/A3 | 70 | 0.0112 | 1241379 | 1.4 | | |
| B-38 | C1/A3 | 70 | 0.0103 | 1220134 | 1.4 | | |
| B-39 | C2/A3 | 70 | 0.0123 | 1001408 | 1.4 | | |
| B-40 | C2/A3 | 70 | 0.0128 | 1006577 | 1.5 | | |
| B-41 | C2/A3 | 70 | 0.0109 | 896320 | 1.5 | | |
| B-42 | C1/A2 | 70 | 0.0353 | 696371 | 1.5 | | |
| B-43 | C1/A2 | 70 | 0.036 | 722538 | 1.5 | | |
| B-44 | C1/A2 | 70 | 0.0461 | 666835 | 1.5 | | |
| B-45 | C1/A2 | 70 | 0.0425 | 723357 | 1.6 | | |
| B-46 | C2/A2 | 70 | 0.029 | 813853 | 1.5 | | |
| B-47 | C2/A2 | 70 | 0.0253 | 831702 | 1.5 | | |
| B-48 | C2/A2 | 70 | 0.0244 | 881734 | 1.5 | | |
| B-49 | C2/A2 | 70 | 0.0274 | 948407 | 1.5 | | |
| B-50 | Comp1/A1 | 100 | 0.0354 | 46933 | 1.4 | | |
| B-51 | Comp1/A1 | 100 | 0.0168 | 52225 | 1.4 | | |
| B-52 | Comp1/A1 | 100 | 0.0283 | 49153 | 1.4 | | |
| B-53 | Comp1/A1 | 100 | 0.0451 | 46804 | 1.4 | | |
| B-54 | Comp1/A1 | 100 | 0.0445 | 48045 | 1.4 | | |
| B-55 | Comp1/A1 | 100 | 0.0329 | 47905 | 1.4 | 122 | 40 |
| B-56 | Comp1/A1 | 100 | 0.0307 | 50826 | 1.4 | | |
| B-57 | Comp1/A1 | 100 | 0.0395 | 45812 | 1.4 | | |
| B-58 | Comp2/A1 | 100 | 0.0398 | 62064 | 1.4 | 148 | 80 |
| B-59 | Comp2/A1 | 100 | 0.0554 | 55896 | 1.5 | 151 | 106 |
| B-60 | Comp2/A1 | 100 | 0.0685 | 56767 | 1.5 | | |
| B-61 | Comp2/A1 | 100 | 0.069 | 53370 | 1.5 | | |
| B-62 | C2/A1 | 100 | 0.0161 | 155070 | 1.5 | | |
| B-63 | C2/A1 | 100 | 0.0192 | 199260 | 1.5 | | |
| B-64 | C2/A1 | 100 | 0.0266 | 173242 | 1.4 | | |
| B-65 | C1/A1 | 100 | 0.0254 | 195451 | 1.4 | | |
| B-66 | C1/A1 | 100 | 0.0344 | 183654 | 1.4 | 128 | 70 |
| B-67 | C1/A1 | 100 | 0.0349 | 168068 | 1.4 | 126 | 69 |

TABLE 6

Example B. Summary of Batch Propylene Polymerization Data

| Metallocene/Activator | Temp (° C.) | Avg Mw (g/mol) | Std Dev Mw (g/mol) | Number of Experiments |
|---|---|---|---|---|
| C1/A1 | 40 | 2105520 | | 1 |
| C2/A1 | 40 | 2220150 | 226800 | 4 |
| Comp1/A1 | 40 | 665105 | 19646 | 4 |
| Comp2/A1 | 40 | 1237555 | | 1 |
| C1/A1 | 70 | 766436 | 63812 | 4 |
| C1/A2 | 70 | 702275 | 26745 | 4 |
| C1/A3 | 70 | 1230756 | 15022 | 2 |
| C2/A1 | 70 | 991483 | 35315 | 4 |
| C2/A2 | 70 | 868924 | 60277 | 4 |
| C2/A3 | 70 | 968102 | 62218 | 3 |
| Comp1/A1 | 70 | 208641 | 10025 | 14 |
| Comp2/A1 | 70 | 263464 | 11438 | 4 |
| C1/A1 | 100 | 182391 | 13735 | 3 |
| C2/A1 | 100 | 175857 | 22211 | 3 |
| Comp1/A1 | 100 | 48463 | 2165 | 8 |
| Comp2/A1 | 100 | 57024 | 3656 | 4 |

TABLE 7A

Examples C1-C9. Feed Conditions for Copolymerizations Using C1/A1

| | Ex. | | | | | | | | |
|---|---|---|---|---|---|---|---|---|---|
| | C1 | C2 | C3 | C4 | C5 | C6 | C7 | C8 | C9 |
| Hexane (mL/min) | 90 | 90 | 90 | 90 | 90 | 90 | 90 | 90 | 90 |
| Ethylene (g/min) | 0.895 | 1.12 | 1.12 | 0.783 | 0.94 | 1.436 | 1.35 | 1.25 | 1.5 |
| Propylene (g/min) | 13.52 | 13.52 | 13.52 | 9.47 | 9.47 | 13.52 | 13.52 | 13.52 | 16.23 |
| Temp (° C.) | 90 | 90 | 90 | 90 | 120 | 90 | 90 | 90 | 90 |
| Cat. (mL/min) | 0.75 | 0.75 | 0.75 | 0.75 | 0.75 | 0.6 | 0.45 | 0.35 | 0.35 |
| TNOA (mL/min) | 1.5 | 1.5 | 1.5 | 1.5 | 1.5 | 1.5 | 1.5 | 1.5 | 1.5 |

TABLE 7b

Examples C1-C9. Polymerization Results for Copolymerizations Using C1/A1

| | Ex. | | | | | | | | |
|---|---|---|---|---|---|---|---|---|---|
| | C1 | C2 | C3 | C4 | C5 | C6 | C7 | C8 | C9 |
| Polym. Rate (g/h) | 453.6 | 507.9 | 418.4 | 346.2 | 383.7 | 478.4 | 449.3 | 469.0 | 562.4 |
| C2 content (wt %) | 10.21 | 12.45 | 13.09 | 11.64 | 11.6 | 16.56 | 15.71 | 14.88 | 14.31 |
| Conc.$^a$ (wt %) | 12.49 | 12.38 | 11.67 | 8.42 | 10.99 | 11.93 | 11.84 | 11.43 | 13.62 |
| Mn (g/mol) | 36556 | 34935 | 56225 | 46493 | 15398 | 47647 | 43892 | 42204 | 40660 |
| Mw (g/mol) | 72674 | 56755 | 88920 | 70119 | 31654 | 85523 | 76746 | 75516 | 72532 |
| dHf$^b$ (J/g) | 26.8 | 25.3 | 23.6 | 31.5 | 7.7 | 6.3 | 13.3 | 19.8 | 18.2 |
| Tm (° C.) | 43 | 43 | 43 | 43 | 45 | 48 | 47 | 45 | 44 |

$^a$Polymer concentration in solvent.
$^b$Heat of fusion.

TABLE 8A

Examples D1-D3. Feed conditions for Copolymerizations Using C2/A1

| Ex. | D1 | D2 | D3 |
|---|---|---|---|
| Hexane (mL/min) | 90 | 90 | 90 |
| Ethylene (g/min) | 0.895 | 1.12 | 1.12 |
| Propylene (g/min) | 13.525 | 13.525 | 13.525 |
| Temp (° C.) | 90 | 90 | 60 |
| Cat. (mL/min) | 0.75 | 0.75 | 0.75 |
| TNOA (mL/min) | 1.5 | 1.5 | 1.5 |

TABLE 8b

Examples D1-D3. Polymerization Results for Copolymerizations Using C2/A1

| Ex. | D1 | D2 | D3 |
|---|---|---|---|
| Polym. Rate (g/h) | 431.4 | 429.4 | 351.2 |
| C2 content (wt %) | 10.53 | 12.97 | 13.33 |
| Conc.$^a$ (wt %) | 11.67 | 10.63 | 9.78 |
| Mn (g/mol) | 58191 | 55007 | 94382 |
| Mw (g/mol) | 96793 | 96062 | 157313 |
| dHf$^b$ (J/g) | 39.3 | 20.5 | 23.1 |
| Tm (° C.) | 43 | 44 | 43 |

$^a$Polymer concentration in solvent.
$^b$Heat of fusion.

TABLE 9A

Examples E1-E8. Feed Conditions for Copolymerizations Using C2/A1

| | Ex. | | | | | | | |
|---|---|---|---|---|---|---|---|---|
| | E1 | E2 | E3 | E4 | E5 | E6 | E7 | E8 |
| Hexane (mL/min) | 90 | 90 | 90 | 90 | 90 | 90 | 90 | 90 |
| Ethylene (g/min) | 1.44 | 1.35 | 1.25 | 1.52 | 1.44 | 1.35 | 1.25 | 1.35 |
| Propylene (g/min) | 13.53 | 13.53 | 13.53 | 16.23 | 13.53 | 13.53 | 13.53 | 16.23 |
| Temp (° C.) | 90 | 90 | 90 | 90 | 70 | 70 | 70 | 70 |
| Cat. (mL/min) | 1.2 | 0.9 | 0.7 | 0.7 | 1.2 | 0.9 | 0.7 | 0.7 |
| TNOA (mL/min) | 1.5 | 1.5 | 1.5 | 1.5 | 1.5 | 1.5 | 1.5 | 1.5 |

TABLE 9b

Examples E1-E8. Polymerization Results for Copolymerizations Using C2/A1

| | Ex. | | | | | | | |
|---|---|---|---|---|---|---|---|---|
| | E1 | E2 | E3 | E4 | E5 | E6 | E7 | E8 |
| Polym. Rate (g/h) | 453.9 | 422.6 | 325.5 | 341.82 | 389.4 | 323.9 | 254.3 | 355.07 |
| C2 content (wt %) | 16.11 | 16.02 | 16.57 | 19.72 | 17.11 | 17.65 | 17.73 | 15.15 |
| Conc.$^a$ (wt %) | 11.23 | 11.79 | 9.83 | 8.86 | 10.93 | 9.09 | 7.14 | 9.96 |
| Mn (g/mol) | 55595 | 60736 | 64667 | 66848 | 100133 | 79530 | 84668 | 89135 |
| Mw (g/mol) | 108773 | 112539 | 117315 | 117138 | 209073 | 146609 | 154093 | 160616 |
| dHf$^b$ (J/g) | 7.6 | 8.2 | 7.6 | 1.0 | 4.2 | 1.3 | 0.98 | 11.5 |
| Tm (° C.) | 46 | 47 | 47 | 48 | 47 | 47 | 49 | 45 |

$^a$Polymer concentration in solvent.
$^b$Heat of fusion.

TABLE 10A

Examples F1-F4. Feed Conditions for Copolymerizations Using C1/A3

| Ex. | F1 | F2 | F3 | F4 |
|---|---|---|---|---|
| Hexane (mL/min) | 90 | 90 | 90 | 90 |
| Ethylene (g/min) | 1.436 | 1.35 | 1.25 | 1.6 |
| Propylene (g/min) | 13.525 | 13.525 | 13.525 | 16.23 |
| Temp (° C.) | 90 | 90 | 90 | 90 |
| Cat. (mL/min) | 1.2 | 0.9 | 0.7 | 0.7 |
| TNOA (mL/min) | 1.5 | 1.5 | 1.5 | 1.5 |

TABLE 11A

Examples G1-G3. Feed Conditions for Copolymerizations Using C1/A3

| Ex. | G1 | G2 | G3 |
|---|---|---|---|
| Hexane (mL/min) | 90 | 90 | 90 |
| Ethylene (g/min) | 1.52 | 1.45 | 1.35 |
| Propylene (g/min) | 16.23 | 16.23 | 16.23 |
| Temp (° C.) | 90 | 90 | 90 |
| Cat. (mL/min) | 1.2 | 0.9 | 0.7 |
| TNOA (mL/min) | 1.5 | 1.5 | 1.5 |

TABLE 10B

Examples F1-F4. Polymerization Results for Copolymerizations Using C1/A3

| Ex. | F1 | F2 | F3 | F4 |
|---|---|---|---|---|
| Polym. Rate (g/h) | 485.2 | 455.7 | 381.2 | 475.3 |
| C2 content (wt %) | 16.23 | 16.38 | 16.32 | 16.52 |
| Conc.$^a$ (wt %) | 14.13 | 12.70 | 10.81 | 14.37 |
| Mn (g/mol) | 49984 | 53889 | 55427 | 55951 |
| Mw (g/mol) | 91650 | 97287 | 100107 | 100309 |
| dHf$^b$ (J/g) | 10 | 12.5 | 11.4 | 8.6 |
| Tm (° C.) | 48 | 47 | 46 | 50 |

$^a$Polymer concentration insolvent.
$^b$Heat of fusion.

TABLE 11b

Examples G1-G3. Polymerization Results for Copolymerizations Using C1/A3

| Ex. | G1 | G2 | G3 |
|---|---|---|---|
| Polym. Rate (g/h) | 333.58 | 218.94 | 167.72 |
| C2 content (wt %) | 18.59 | 20.82 | 20.76 |
| Conc.$^a$ (wt %) | 10.07 | 7.21 | 5.53 |
| Mn (g/mol) | 64877 | 67506 | 70690 |
| Mw (g/mol) | 139060 | 147172 | 153268 |
| dHf$^b$ (J/g) | 3.6 | 1 | 1.9 |
| Tm (° C.) | 47 | 47 | 47 |

$^a$Polymer concentration in solvent.
$^b$Heat of fusion.

TABLE 12A

Examples H1-H8. Feed Conditions for Copolymerizations Using C2/A3

| | Ex. | | | | | | | |
|---|---|---|---|---|---|---|---|---|
| | H1 | H2 | H3 | H4 | H5 | H6 | H7 | H8 |
| Hexane (mL/min) | 90 | 90 | 90 | 90 | 90 | 90 | 90 | 90 |
| Ethylene (g/min) | 1.436 | 1.35 | 1.25 | 1.6 | 1.436 | 1.35 | 1.25 | 1.35 |
| Propylene (g/min) | 13.525 | 13.525 | 13.525 | 16.23 | 13.525 | 13.525 | 13.525 | 16.23 |
| Temp (° C.) | 90 | 90 | 90 | 90 | 70 | 70 | 70 | 70 |
| Cat. (mL/min) | 1.2 | 0.9 | 0.7 | 0.7 | 1.2 | 0.9 | 0.7 | 0.7 |
| TNOA (mL/min) | 1.5 | 1.5 | 1.5 | 1.5 | 1.5 | 1.5 | 1.5 | 1.5 |

TABLE 12b

Examples H1-H8. Polymerization Results for Copolymerizations Using C2/A3

| | Ex. | | | | | | | |
|---|---|---|---|---|---|---|---|---|
| | H1 | H2 | H3 | H4 | H5 | H6 | H7 | H8 |
| Polym. Rate (g/h) | 400.3 | 373.9 | 301.9 | 362.92 | 404.8 | 286.1 | 277.3 | 258.39 |
| C2 content (wt %) | 17.08 | 16.91 | 16.99 | 18.51 | 18.85 | 0.75 | 18.93 | 18.56 |
| Conc.$^a$ (wt %) | 11.73 | 11.68 | 9.345 | 10.87 | 7.43 | 48.5 | 7.22 | 6.76 |
| Mn (g/mol) | 65852 | 64015 | 68412 | 73549 | 116409 | 93779 | 102761 | 109127 |
| Mw (g/mol) | 119694 | 121598 | 160803 | 165140 | 205548 | 150839 | 160747 | 166821 |
| dHf$^b$ (J/g) | 7.6 | 8.2 | 7.6 | 1 | 22.95 | 0.52 | 0.48 | 2.94 |
| Tm (° C.) | 48 | 48 | 48 | 48 | 43.1 | 48 | 48.5 | 49.7 |

$^a$Polymer concentration in solvent.
$^b$Heat of fusion.

TABLE 13a

Feed Conditions for Copolymerization Using C4/A1.

| | Ex. | | |
|---|---|---|---|
| | I1 | I2 | I3 |
| Hexane (mL/min) | 90 | 90 | 90 |
| Ethylene (g/min) | 1.44 | 1.43 | 1.44 |
| Propylene (g/min) | 14.38 | 14.8238 | 16.88 |
| Temp (° C.) | 70 | 70 | 90 |
| Cat. (mL/min) | 1.94 | 2.0 | 1.75 |
| TNOA (mL/min) | 1.5 | 1.5 | 1.5 |

TABLE 13b

Examples I1-I3. Polymerization Results for Copolymerizations Using C4/A1

| | Ex. | | |
|---|---|---|---|
| | I1 | I2 | I3 |
| Polym. Rate (g/h) | 588 | 458 | 319 |
| C2 content (wt %) | 19.2 | 19.5 | 21.6 |
| Conc.$^a$ (Wt %) | 14.2 | 11.38 | 8.23 |
| Mn (g/mol) | low | low | low |
| Mw (g/mol) | low | low | low |
| dHf$^b$ (J/g) | 1 | 1 | na |
| Tm (° C.) | 48 | 48 | na |

$^a$Polymer concentration in solvent.
$^b$Heat of fusion.

TABLE 14a

Examples J1-J4.: Feed Conditions for Copolymerization Using C3/A1.

| | Ex. | | | |
|---|---|---|---|---|
| | J1 | J2 | J3 | J4 |
| Hexane (mL/min) | 90 | 90 | 90 | 90 |
| Ethylene (g/min) | 1.077 | 1.35 | 1.35 | 1.35 |
| Propylene (g/min) | 13.53 | 15.01 | 14.58 | 16.23 |
| Temp (° C.) | 70 | 70 | 70 | 70 |
| Cat. (mL/min) | 2.0 | 1.5 | 1.9 | 2.4 |
| TNOA (mL/min) | 1.5 | 1.5 | 1.5 | 1.5 |

TABLE 14b

Examples J1-J4. Polymerization Results for Copolymerizations Using C3/A1

| | Ex. | | | |
|---|---|---|---|---|
| | J1 | J2 | J3 | J4 |
| Polym. Rate (g/h) | 319 | 380 | 351 | 419 |
| C2 content (wt %) | 20.03 | 23.3 | 22.7 | 21.99 |
| Conc.$^a$ (wt %) | 8.23 | 9.64 | 8.98 | 10.54 |
| Mn (g/mol) | low | low | low | low |
| Mw (g/mol) | low | low | low | low |
| dHf$^b$ (J/g) | na | 1 | na | na |
| Tm (° C.) | na | 48 | na | na |

$^a$polymer concentration in solvent.
$^b$Heat of fusion.

TABLE 15a

Examples K1-K11. Feed Conditions for Continuous Ethylene Propylene Copolymerizations Employing C2/A1

| Example | Polym. Temp (° C.) | C2 rate (Kg/h) | C3 rate (Kg/h) | C6 rate (Kg/h) | cat/act (mol/mol) | Scav/Cat (mol/mol) |
|---|---|---|---|---|---|---|
| K1 | 142.0 | 10.50 | 5.94 | 74.42 | 1.0 | 11.3 |
| K2 | 141.4 | 10.50 | 6.88 | 74.42 | 1.0 | 17.7 |
| K3 | 141.6 | 10.00 | 11.76 | 76.35 | 1.0 | 18.5 |
| K4 | 66.0 | 2.10 | 24.98 | 90.10 | 1.0 | 16.1 |
| K5 | 66.0 | 1.89 | 26.63 | 90.24 | 1.0 | 19.0 |
| K6 | 66.0 | 1.58 | 27.82 | 90.36 | 1.0 | 19.0 |
| K7 | 67.0 | 1.99 | 18.84 | 89.67 | 1.0 | 22.4 |
| K8 | 67.0 | 2.76 | 27.90 | 90.04 | 1.0 | 38.5 |
| K9 | 66.0 | 2.88 | 27.84 | 89.96 | 1.0 | 36.9 |
| K10 | 70.0 | 2.06 | 24.20 | 90.03 | 1.0 | 26.3 |
| K11 | 70.0 | 2.75 | 18.90 | 89.93 | 1.0 | 28.2 |

TABLE 15b

Examples K1-K11. Polymerization Results for Continuous Ethylene Propylene Copolymerizations Employing C2/A1

| Ex. | Poly Rate (Kg/h) | Cat Efficiency (g Pol/g cat) | wt % C2[a] | [mm][a] | m/r[a] (EPPE) | Inversions per 1000C[a] | r1r2[a] | Mw[b] (g/mol) | Mn[c] (g/mol) | Mw[b]/Mn[c] |
|---|---|---|---|---|---|---|---|---|---|---|
| K1 | 10.1 | 106359 | 75.8 | | 4.3 | | 0.45 | 123876 | 46343 | 2.67 |
| K2 | 10.3 | 128142 | 73.9 | | 3.8 | | 0.49 | 115976 | 39420 | 2.94 |
| K3 | 11.7 | 151910 | 61.3 | | 5.1 | | 0.54 | 76895 | 28620 | 2.69 |
| K4 | 9.6 | 199518 | 12.7 | 89.3 | | 3.5 | 0.78 | 187044 | 79186 | 2.36 |
| K5 | 10.0 | 176887 | 10.8 | 89.3 | | 4.2 | 0.79 | 192584 | 98610 | 1.95 |
| K6 | 10.2 | 181331 | 8.0 | 90.4 | | 3.6 | 0.89 | 207560 | 82134 | 2.53 |
| K7 | 9.6 | 151008 | 13.5 | 91.2 | | 3.8 | 0.79 | 155025 | 76753 | 2.02 |
| K8 | 10.5 | 283609 | 13.8 | 91.4 | | 3.9 | 0.69 | 180593 | 89364 | 2.02 |
| K9 | 10.2 | 263865 | 14.3 | 88.4 | | 4.1 | 0.74 | 211564 | 105927 | 2.00 |
| K10 | 10.6 | 196203 | 11.9 | 90.2 | | 3.5 | 0.79 | 169106 | 82310 | 2.05 |
| K11 | 9.6 | 189528 | 18.1 | 91 | | 3.3 | 0.71 | 150801 | 77043 | 1.96 |

[a]Determined from $^{13}C\{^{1}H\}$NMR measurements.
[b]Determined using a light scattering detector.
[c]Determined using a differential refractive index detector.

TABLE 16a

Feed Conditions for Supported Propylene Polymerizations

| Example | Metallocene | Condition | $H_2/N_2$ (psig) | Propylene (mL) | Hexane (mL) | TNOAL (mL) | Catalyst Slurry (mL) |
|---|---|---|---|---|---|---|---|
| L1 | C5 | A | 54.7 | 4.3 | 0.7 | 0.04 | 0.03 |
| L2 | C5 | B | 54.7 | 4.3 | 0.7 | 0.04 | 0.04 |
| L3 | C5 | C | 54.7 | 4.3 | 0.7 | 0.04 | 0.05 |
| L4 | C5 | D | 54.7 | 4.3 | 0.7 | 0.04 | 0.06 |
| L5 | C5 | E | 54.7 | 4.3 | 0.7 | 0.04 | 0.07 |
| L6 | C5 | F | 54.7 | 4.3 | 0.7 | 0.04 | 0.08 |
| L7 | C5 | G | 54.7 | 4.3 | 0.7 | 0.04 | 0.09 |
| L8 | C5 | H | 54.7 | 4.3 | 0.7 | 0.04 | 0.1 |
| L9 | Comp3 | A | 54.7 | 4.3 | 0.7 | 0.04 | 0.03 |
| L10 | Comp3 | B | 54.7 | 4.3 | 0.7 | 0.04 | 0.04 |
| L11 | Comp3 | C | 54.7 | 4.3 | 0.7 | 0.04 | 0.05 |
| L12 | Comp3 | D | 54.7 | 4.3 | 0.7 | 0.04 | 0.06 |
| L13 | Comp3 | E | 54.7 | 4.3 | 0.7 | 0.04 | 0.07 |
| L14 | Comp3 | F | 54.7 | 4.3 | 0.7 | 0.04 | 0.08 |
| L15 | Comp3 | G | 54.7 | 4.3 | 0.7 | 0.04 | 0.09 |
| L16 | Comp3 | H | 54.7 | 4.3 | 0.7 | 0.04 | 0.1 |

TABLE 16b

Supported Propylene Polymerization Data

| Example | Metallocene | Condition | Yield (g) | Mw (g/mol) | Mn (g/mol) | Mw/Mn |
|---|---|---|---|---|---|---|
| L1 | C5 | A | 0.018 | 512844 | 246721 | 2.08 |
| L2 | C5 | B | 0.0224 | 578900 | 312660 | 1.85 |
| L3 | C5 | C | 0.0354 | 534760 | 296029 | 1.81 |
| L4 | C5 | D | 0.0419 | 560049 | 313920 | 1.78 |
| L5 | C5 | E | 0.0205 | 934851 | 446849 | 2.09 |
| L6 | C5 | F | 0.0321 | 662337 | 374585 | 1.77 |
| L7 | C5 | G | 0.0325 | 626450 | 356518 | 1.76 |
| L8 | C5 | H | 0.0445 | 568224 | 319236 | 1.78 |
| L9 | Comp3 | A | 0.0391 | 473241 | 206032 | 2.30 |
| L10 | Comp3 | B | 0.0673 | 220344 | 115631 | 1.91 |
| L11 | Comp3 | C | 0.0954 | 183047 | 102653 | 1.78 |
| L12 | Comp3 | D | 0.174 | 209586 | 113992 | 1.84 |
| L13 | Comp3 | E | 0.2088 | 266103 | 138948 | 1.92 |
| L14 | Comp3 | F | 0.224 | 230346 | 129264 | 1.78 |
| L15 | Comp3 | G | 0.2338 | 228364 | 125242 | 1.82 |
| L16 | Comp3 | H | 0.2519 | 294877 | 167917 | 1.76 |

TABLE 17

Stress Strain Behaviour of EP Copolymers Prepared in Continuous Solution Copolymerizations.

| Sample Example | Youngs Modulus psi | 50% Modulus psi | 100% Modulus psi | 200% Modulus psi | 500% Modulus psi | Ultimate elongation % | Ultimate tensile psi |
|---|---|---|---|---|---|---|---|
| C1 | 335596.2 | 785.06 | 690.67 | 669.82 | 1010.04 | 913.96 | 1774.11 |
| C2 | 93104.45 | 447.94 | 479.27 | 479.11 | 646.25 | 945.4 | 1322.57 |
| C3 | 60267.47 | 430.12 | 461.72 | 468.5 | 749.89 | 857.26 | 1681.33 |
| C6 | 42483.11 | 153.87 | 172.29 | 194.37 | 264.55 | 976.99 | 481.15 |
| C7 | 45406.24 | 192.62 | 220.82 | 251.81 | 336.84 | 976.35 | 620.7 |
| C8 | 44453.35 | 242.35 | 279.26 | 311.28 | 406.8 | 962.46 | 793.66 |
| D2 | 33615.43 | 325.41 | 364.29 | 392.2 | 618.02 | 844.29 | 1408.99 |
| D3 | 23626.48 | 355.89 | 392.11 | 418.27 | 854.01 | 742.17 | 2108.61 |
| E1 | 57684.18 | 127.91 | 138.82 | 143.39 | 180.36 | 953.31 | 373.38 |
| E3 | 41496.2 | 129.53 | 141.22 | 145.1 | 183.61 | 926.93 | 408.98 |
| E4 | 71708.91 | 49.52 | 49.13 | | | 67.91 | 51.17 |
| F2 | 30811.26 | 215.9 | 245.19 | 274.34 | 420.31 | 882.47 | 882.71 |
| G1 | 49528.21 | 93.45 | 99.28 | 96.52 | 99.17 | 1013.42 | 167.55 |
| C3 | 32559.32 | 66.24 | 68.97 | 61.72 | 43.57 | 83.21 | 69.51 |
| H2 | 42393.24 | 126.03 | 137.23 | 141.59 | 185.86 | 903.63 | 413.28 |

TABLE 18

Composition Distribution Determination of EP Copolymers Prepared in Continuous Solution Copolymerizations.

| Sample Ex. | Fraction soluble at 23° C. | | Fraction soluble at 31° C. | | Fraction soluble at 40° C. | | Fraction soluble at 48° C. | | Fraction soluble at 56° C. | |
|---|---|---|---|---|---|---|---|---|---|---|
| | Wt % | C2 wt % | Wt % | C2 wt % | Wt % | C2 wt % | Wt % | C2 wt % | Wt % | C2 wt % |
| C1 | | | | | | | 18.5 | 10 | 82.4 | 10.5 |
| C2 | | | | | 99.3 | 12.6 | | | | |
| C3 | | | | | 99.8 | 13.7 | | | | |
| C6 | 102.3 | 16.3 | | | | | | | | |
| C7 | 101 | 16 | | | | | | | | |
| C8 | 7.2 | 14.7 | 93.6 | 86.9 | | | | | | |
| D2 | | | | | 102 | 12.6 | | | | |
| D3 | | | | | 101.6 | 13.1 | | | | |
| E1 | 101.4 | 16 | | | | | | | | |
| E3 | 101.3 | 16.6 | | | | | | | | |
| E4 | 100.1 | 19.6 | | | | | | | | |
| F2 | 64.1 | 16.1 | 37.1 | 16.2 | | | | | | |
| G1 | 100.1 | 18.2 | | | | | | | | |
| C3 | 100.4 | 20.3 | | | | | | | | |
| H2 | 100.3 | 16.5 | | | | | | | | |

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A composition represented by the formula:

where
M is hafnium or zirconium;
each $R^1$ is methyl;
each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof;
$R^3$ is carbon;
$R^4$ is $CH_2$;
a is 1;
$R^5$ is $CH_2$;
b is 1;
$R^6$ is carbon; and $R^3$, $R^4$, $R^5$ and $R^6$ are bound together to form a ring;
each $R^7$ is hydrogen;
each $R^8$ is hydrogen;
each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{16}$ may be linked together to form a ring, $R^9$ and $R^{11}$ may be linked together to form a ring;
c is 0;
$R^{10}$ is $-M^2(R^{16})_h-$ where $M^2$ is Si, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;
d is 1;
each $R^{11}$ is independently selected from the group consisting of hydrogen, hydrocarbyl, substituted hydrocarbyl and a functional group, and two $R^{11}$ groups may be linked together to form a ring $R^{11}$ and $R^8$ may be linked together to form a ring $R^{11}$ and $R^{16}$ may be linked together to form a ring;
e is 1;
where the sum of c, d, and e is 2;
$R^{12}$ is carbon;
$R^{13}$ is $CH_2$;
f is 1;
$R^{14}$ is $CH_2$;
g is 1; and
$R^{15}$ is carbon.

2. The composition of claim 1 wherein M is zirconium.
3. The composition of claim 1 wherein M is hafnium.
4. The composition of claim 1 wherein $R^2$ is methyl, ethyl or propyl.
5. The composition of claim 1 wherein $R^2$ is methyl or ethyl.
6. The composition of claim 1 wherein $R^9$ is hydrogen, methyl, ethyl, propyl or phenyl.
7. The composition of claim 1 wherein $R^{10}$ is $SiMe_2$, $Si(CH_2)_3$, $SiPh_2$, $Si(biphenyl)_1$, $Si(biphenyl)_2$, $Si(o\text{-tolyl})_2$.
8. The composition of claim 1 wherein $R^{11}$ is hydrogen, methyl, ethyl, propyl or phenyl.

9. A composition represented by the formula:

where
M is hafnium or zirconium;
each $R^1$ is methyl;
each $R^2$ is independently selected from the group consisting of ethyl, propyl, butyl, pentyl, hexyl and the isomers thereof;
each $R^7$ is hydrogen;
each $R^8$ is hydrogen;
each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{11}$ may be linked together to form a ring;
c is 0,1 or 2;
$R^{10}$ is $-M^2(R^{16})_h-$ where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;
d is 0, 1, or 2;
each $R^{11}$ is independently selected from the group consisting of hydrogen, hydrocarbyl, substituted hydrocarbyl and a functional group, and two $R^{11}$ groups may be linked together to form a ring $R^{11}$ and $R^8$ may be linked together to form a ring;
e is 0, 1,or 2;

where the sum of c, d, and e is 1, 2 or 3.

10. A composition represented by the one of the following formulae:

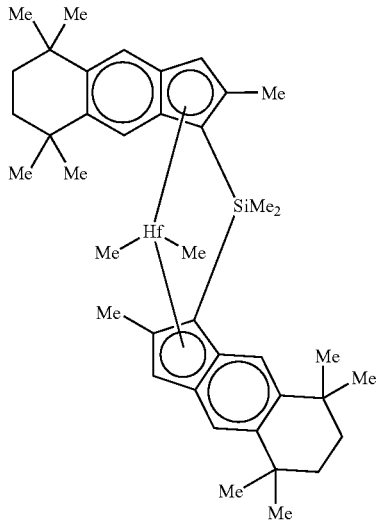

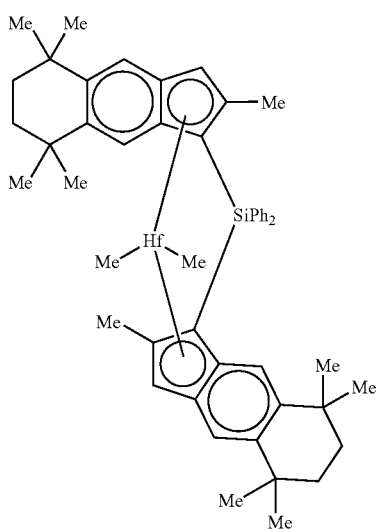

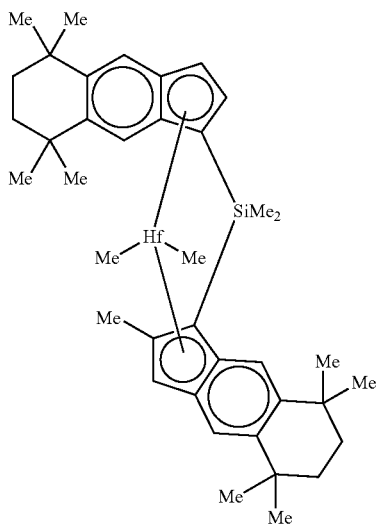

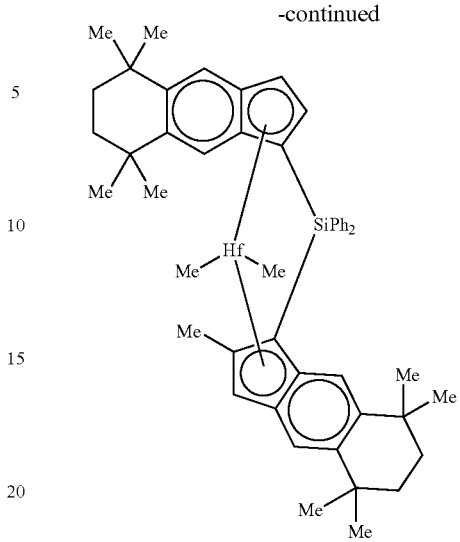

where Me is methyl, Hf is hafnium, Ph is phenyl, and Si is silicon, and an activator.

11. The composition of claim 10 wherein the activator is a Lewis acid that ionizes the bridged metallocene metal center into a cation and provides a counterbalancing noncoordinating ion.

12. The composition of claim 10 wherein the activator is represented by the following formula:

$$(S^{t+})_u(NCA^{v-})_w$$

$S^{t+}$ is a cation component having the charge t+

$NCA^{v-}$ is a non-coordinating anion having the charge v− t is an integer from 1 to 3;

v is an integer from 1 to 3;

u and v are constrained by the relationship: $(u) \times (t) = (v) \times (w)$; where $S^{t+}$ is a Bronsted acids or a reducible Lewis acids capable of protonating or abstracting a moiety.

13. A catalyst system comprising the composition of claim 1 and an activator selected from the group consisting of trimethylammonium tetraphenylborate, triethylammonium tetraphenylborate, tripropylammonium tetraphenylborate, tri (n-butyl)ammonium tetraphenylborate, tri(t-butyl) ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, trimethylammonium tetrakis (heptafluoronaphthyl)borate, triethylammonium tetrakis (heptafluoronaphthyl)borate, tripropylammonium tetrakis (heptafluoronaphthyl)borate, tri(n-butyl)ammonium tetrakis (heptafluoronaphthyl)borate, tri(sec-butyl)ammonium tetrakis(heptafluoronaphthyl)borate, N,N-dimethylanilinium tetrakis(heptafluoronaphthyl)borate, N,N-diethylanilinium tetrakis(heptafluoronaphthyl)borate, trimethylammonium (2-perfluorobiphenyl)$_3$(perfluorophenylalkynyl)borate, triethylammonium (2-perfluorobiphenyl)$_3$(perfluorophenylalkynyl)borate, tripropylammonium (2-perfluorobiphenyl)$_3$ (perfluorophenylalkynyl)borate, tri(n-butyl)ammonium (2-perfluorobiphenyl)₃(perfluorophenylalkynyl)borate, tri(sec-butyl)ammonium (2-perfluorobiphenyl)₃(perfluorophenylalkynyl)borate, N,N-dimethylanilinium (2-perfluorobiphenyl)₃(perfluorophenylalkynyl)borate, N,N-diethylanilinium (2-perfluorobiphenyl)₃(perfluorophenylalkynyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl) borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluoro-phenyl)borate, N,N-dimethyl-(2,4,6-trimethylanilinium)tetrakis-(2,3,4,6-tetrafluorophenyl)borate, di-(i-propyl)ammonium tetrakis(pentafluorophenyl)borate, and dicyclohexylammonium tetrakis(pentafluorophenyl)borate, triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate, triphenylcarbenium tetrakis(pentafluorophenyl)borate, triphenylcarbenium tetrakis(heptafluoronaphthyl)borate, triphenylcarbenium (2-perfluorobiphenyl)₃(perfluorophenylalkynyl)borate, trisperfluorophenyl borane, and triperfluoronaphthyl borane.

14. A catalyst system comprising the composition of claim 1 and an activator selected from the group consisting of N,N-dimethylanilinium tetrakis(perfluorophenyl)borate and triphenylcarbenium tetrakis(perfluorophenyl)borate.

15. A catalyst system comprising the composition of claim 1 and an alumoxane.

16. A catalyst system comprising the composition of claim 1 and methylalumoxane.

\* \* \* \* \*

UNITED STATES PATENT AND TRADEMARK OFFICE
CERTIFICATE OF CORRECTION

PATENT NO. : 7,601,666 B2 Page 1 of 1
APPLICATION NO. : 11/178147
DATED : October 13, 2009
INVENTOR(S) : Rui Zhao It is certified that error appears in the above-identified patent and that said Letters Patent is hereby corrected as shown below:

Title page, item [75] inventor: should be as follows:

Rui Zhao

Signed and Sealed this

Twenty-third Day of February, 2010

David J. Kappos
*Director of the United States Patent and Trademark Office*